US010829557B2

(12) United States Patent
Narwal et al.

(10) Patent No.: US 10,829,557 B2
(45) Date of Patent: *Nov. 10, 2020

(54) ANTI-B7-H1 ANTIBODIES FOR TREATING TUMORS

(71) Applicant: MEDIMMUNE LIMITED, Cambridge (GB)

(72) Inventors: Rajesh Narwal, Gaithersburg, MD (US); David Fairman, Cambridge (GB); Paul Robbins, Gaithersburg, MD (US); Meina Liang, Gaithersburg, MD (US); Amy Schneider, Gaithersburg, MD (US); Carlos Chavez, Gaithersburg, MD (US); Carina Herl, Gaithersburg, MD (US); Min Pak, Gaithersburg, MD (US); Hong Lu, Gaithersburg, MD (US); Marlon Rebelatto, Gaithersburg, MD (US); Keith Steele, Gaithersburg, MD (US); Anmarie Boutrin, Gaithersburg, MD (US); Li Shi, Gaithersburg, MD (US); Shengyan Hong, Gaithersburg, MD (US); Brandon Higgs, Gaithersburg, MD (US); Lorin Roskos, Gaithersburg, MD (US)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/418,488

(22) Filed: May 21, 2019

(65) Prior Publication Data

US 2019/0338033 A1 Nov. 7, 2019

Related U.S. Application Data

(63) Continuation of application No. 15/021,161, filed as application No. PCT/EP2014/069425 on Sep. 11, 2014, now Pat. No. 10,336,823.

(60) Provisional application No. 61/876,509, filed on Sep. 11, 2013, provisional application No. 61/971,212, filed on Mar. 27, 2014, provisional application No. 61/978,401, filed on Apr. 11, 2014, provisional application No. 62/003,349, filed on May 27, 2014.

(51) Int. Cl.
| | | |
|---|---|---|
| C07K 16/28 | (2006.01) |
| A61K 39/395 | (2006.01) |
| C07K 16/30 | (2006.01) |
| G01N 33/574 | (2006.01) |
| A61K 39/00 | (2006.01) |

(52) U.S. Cl.
CPC .......... *C07K 16/2827* (2013.01); *C07K 16/30* (2013.01); *C07K 16/3023* (2013.01); *G01N 33/57492* (2013.01); *A61K 2039/505* (2013.01); *A61K 2039/545* (2013.01); *C07K 2317/21* (2013.01); *C07K 2317/73* (2013.01); *C07K 2317/76* (2013.01); *C07K 2317/94* (2013.01); *G01N 2333/70532* (2013.01)

(58) Field of Classification Search
None
See application file for complete search history.

(56) References Cited

U.S. PATENT DOCUMENTS

| 10,232,040 | B2 * | 3/2019 | Narwal | ................... A61P 35/04 |
|---|---|---|---|---|
| 10,336,823 | B2 * | 7/2019 | Narwal | .............. C07K 16/3023 |
| 2010/0285039 | A1 | 11/2010 | Chen | |
| 2013/0034559 | A1 | 2/2013 | Queva | |
| 2015/0328311 | A1 | 11/2015 | Narwal | |
| 2016/0051672 | A1 | 2/2016 | Stewart | |
| 2016/0347848 | A1 | 12/2016 | Hammond | |
| 2017/0275347 | A1 | 9/2017 | Higgs | |
| 2017/0306025 | A1 | 10/2017 | Du | |
| 2017/0320954 | A1 | 11/2017 | Barry | |
| 2017/0327588 | A1 | 11/2017 | Baca | |

FOREIGN PATENT DOCUMENTS

| EP | 2172219 | 7/2010 |
|---|---|---|
| WO | WO2011/066389 | 3/2011 |
| WO | WO2013/079174 | 6/2013 |

OTHER PUBLICATIONS

Weight Percentile Calculator for Men and Women in the United States (https://dqydj.com/weight-percentile-calculator-men-women) accessed on Oct. 30, 2019; 7 pages.*
AstraZeneca Global, "AstraZeneca initiates phase III immunotherapy study for MEDI4736 in patients with lung cancer," May 8, 2014, XP002733499, Retrieved from the Internet: URL:http://www.astrazeneca.com/Media/Press-releases/Article/20140508-astrazeneca-initiates-phase-iii-immunotherapy-study-MEDI4736.
Villaruz L, et al., "Immunotherapy in lung cancer," Transl. Lung Cancer Res., vol. 3, No. 1, Feb. 1, 2014, pp. 2-14.
Lutzky, J., et al., "A phase 1 study of MEDI4736, an anti-Pd-L1 antibody, in patients with advanced solid tumors," Journal of clinical oncology, vol. 32, No. 15 Suppl., May 20, 2014, p. 3001.
Medimmune, LLC, "A phase 1/2 Study to Evaluate MEDI4736," Clinical Trials, Sep. 14, 2012, Retrieved from the internet: URL:http://clinicaltrials.gov/ct2/show/NCT01693562.
Sheng, Y. et al., "Advances in targeting cell surface signalling molecules for immune modulation," Nature Reviews Drug Discovery, vol. 12, No. 2., Feb. 1, 2013, pp. 130-146.
International Preliminary Report on Patentability based on International Application No. PCT/EP2014/069425, dated Mar. 15, 2016.
International Search Report based on International Application No. PCT/EP2014/069425, dated May 1, 2015.
Written Opinion of the International Searching Authority based on International Application No. PCT/EP2014/069425.

(Continued)

*Primary Examiner* — Ilia I Ouspenski

(57) ABSTRACT

Provided herein are methods of treating B7-H1-expressing tumors comprising administering an effective amount of MEDI4736 or an antigen-binding fragment thereof.

9 Claims, 28 Drawing Sheets

Specification includes a Sequence Listing.

(56) References Cited

OTHER PUBLICATIONS

Sanderson, et al., BMJ. 2002; 325, pp. 822-827.
Brahmer, et al., N. Engl. J. Med. 2012; 366, pp. 2455-2465.
Reungwetwattana, et al., J. Carcinog. 2013; 12: 22.
Topalian, et al., N. Engl. J. Med. 2012; 366, pp. 2443-2454.

* cited by examiner

Baseline demographics and disease characteristics

| Characteristic | 0.1 mg/kg (n=4) | 0.3 mg/kg (n=4) | 1 mg/kg (n=3) | 3 mg/kg (n=3) | 10 mg/kg (n=13) | Total (n=27) | Expansion (n=6) |
|---|---|---|---|---|---|---|---|
| Mean age, years (range) | 58.5 (48–65) | 68.0 (65–71) | 65.3 (43–77) | 57.0 (42–69) | 57.7 (35–76) | — | 61.8 (41–78) |
| Sex, n, male/female | 2/2 | 3/1 | 1/2 | 1/2 | 6/7 | 13/14 | 4/2 |
| ECOG PS at baseline, n | | | | | | | |
| 0 | 2 | 1 | 2 | 0 | 3 | 8 | 2 |
| 1 | 2 | 3 | 1 | 3 | 9 | 18 | 4 |
| Median prior cancer treatments, n (range) | 6.0 (4–10) | 3.5 (3–4) | 4.0 (1–6) | 3.0 (1–4) | 4.0 (1–6) | — | 2.4 (2–5) |
| Tumor type, n | | | | | | | |
| CRC | 0 | 1 | 0 | 1 | 0 | 2 | 0 |
| Melanoma | 1 | 0 | 1 | 0 | 2 | 4 | 5 |
| NSCLC non-squamous | 3 | 2 | 2 | 1 | 9 | 17 | 1 |
| NSCLC squamous | 0 | 1 | 0 | 1 | 0 | 2 | 0 |
| RCC | 0 | 0 | 0 | 0 | 2 | 2 | 0 |

Figure 3

Pharmacokinetics of MEDI4736

| Dose of MEDI4736 (mg/kg) IV | Human AUC(inf) (d·µg/mL) | Safety Margin (AUCm/AUCh) | Actual human Cmax (µg/mL) | Safety Margin ($C_{max}m/C_{max}h$) |
|---|---|---|---|---|
| 0.1 | 6 | 4733 | 2.8 | 1357 |
| 0.3 | 28 | 1014 | 8.0 | 475 |

Figure 4

MEDI4736 Clinical Activity

| MEDI4736 Dose Level | Patient | Tumor Type | Number of Doses Received | Best Response (irRC) | % Change in Tumor Burden |
|---|---|---|---|---|---|
| 0.1 mg/kg Q2W | 1056201004 | NSCLC | 18+ | SD | -47.6% |
| 0.1 mg/kg Q2W | 1056201006 | NSCLC | 11 | PD | +50.3% |
| 0.1 mg/kg Q2W | 1245501002 | NSCLC | 3 | NE | NE |
| 0.1 mg/kg Q2W | 1245501003 | Melanoma | 8 | PD | +55.8 |
| 0.3 mg/kg Q2W | 1094301002 | CRC | 5 | PD | +>100% |
| 0.3 mg/kg Q2W | 1245501006 | NSCLC | 12+ | SD | -60.1% |
| 0.3 mg/kg Q2W | 1351901002 | NSCLC | 1 | NE | NE |
| 0.3 mg/kg Q2W | 1351901004 | NSCLC | 11+ | SD | -34.1% |
| 1.0 mg/kg Q2W | 1056201009 | NSCLC | 8+ | SD | -42.2% |
| 1.0 mg/kg Q2W | 1094301003 | NSCLC | 9+ | PR | -83.1% |
| 1.0 mg/kg Q2W | 1351901007 | Melanoma | 8+ | PR | -69.1% |

*Patient 1056201004 received prophylactic steroids prior to dosing.

Figure 7

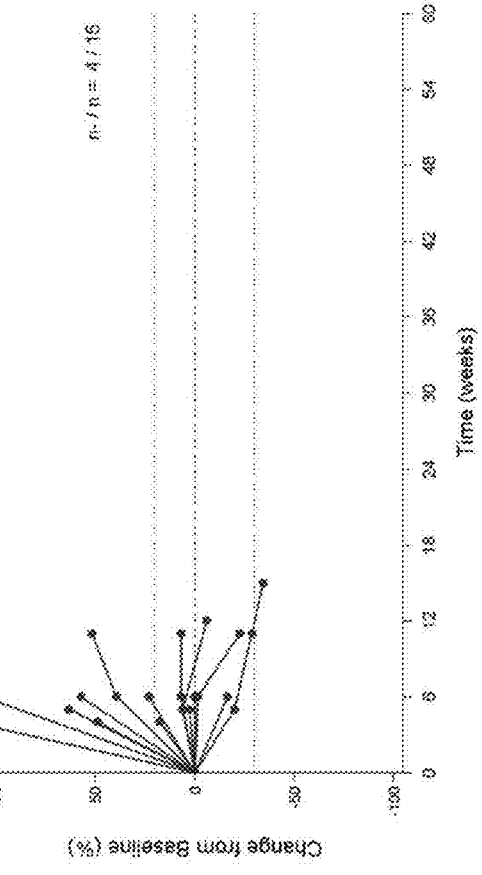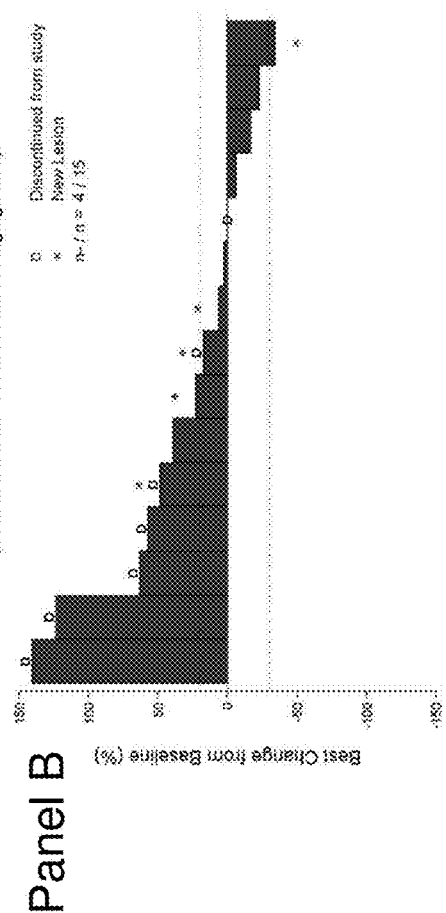
Figure 13

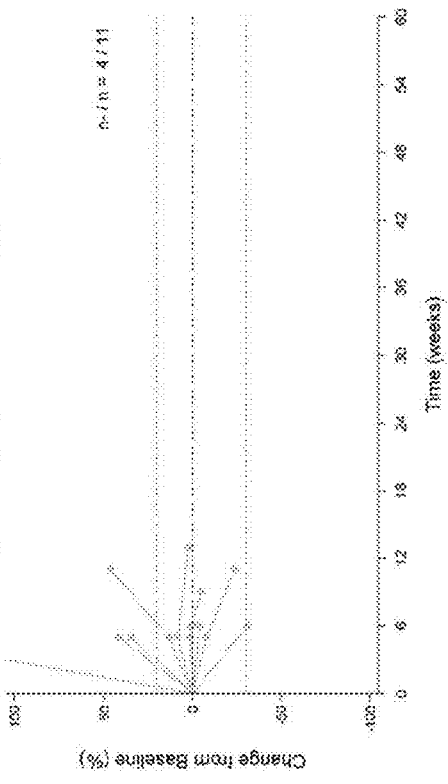
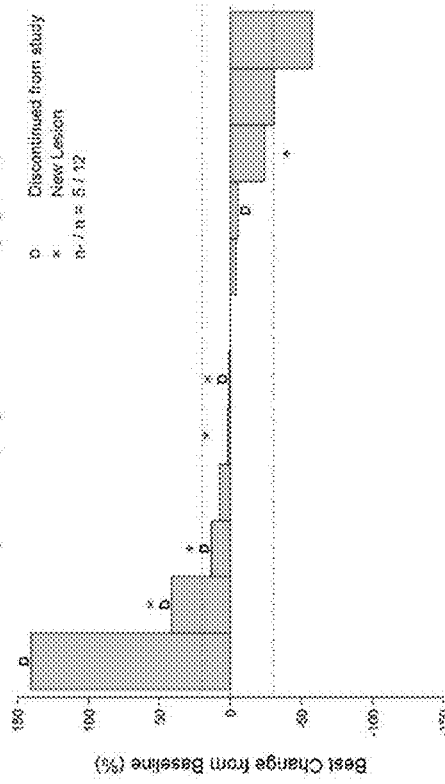
Figure 14A&B

ANTI-B7-H1 ANTIBODIES FOR TREATING TUMORS

REFERENCE TO THE SEQUENCE LISTING

This application incorporates by reference a Sequence Listing submitted with this application as text file entitled B7H1-200-US1_SL.TXT created on Mar. 7, 2016 and having a size of 13.4 megabytes.

BACKGROUND

Cancer continues to be a major global health burden. Despite progress in the treatment of cancer, there continues to be an unmet medical need for more effective and less toxic therapies, especially for those patients with advanced disease or cancers that are resistant to existing therapeutics.

The immune system is capable of identifying tumor-associated antigens and eliminating the cancerous cells expressing them. This process of tumor immune surveillance, or tumor immunoediting, plays an important role in preventing and combating the growth of tumors, and levels of tumor-infiltrating lymphocytes, and more specifically cytotoxic T cells, have been correlated to improved prognosis in a number of cancers. Thus, enhancing the immune response may provide a means to control tumors.

B7-H1 (also known as programmed death ligand 1 (PD-L1) or CD274) is part of a complex system of receptors and ligands that are involved in controlling T-cell activation. In normal tissue, B7-H1 is expressed on T cells, B cells, dendritic cells, macrophages, mesenchymal stem cells, bone marrow-derived mast cells, as well as various nonhematopoietic cells. Its normal function is to regulate the balance between T-cell activation and tolerance through interaction with its two receptors: programmed death 1 (also known as PD-1 or CD279) and CD80 (also known as B7-1).

B7-H1 is also expressed by tumors and acts at multiple sites to help tumors evade detection and elimination by the host immune system. B7-H1 is expressed in a broad range of cancers with a high frequency. In some cancers, expression of B7-H1 has been associated with reduced survival and unfavorable prognosis. Antibodies that block the interaction between B7-H1 and its receptors are able to relieve B7-H1-dependent immunosuppressive effects and enhance the cytotoxic activity of antitumor T cells in vitro.

MEDI4736 is a human monoclonal antibody directed against human B7-H1 that is capable of blocking the binding of B7-H1 to both the PD-1 and CD80 receptors. Thus, given the high unmet need of treating tumors, including those with a high incidence rate as well as less common types with limited treatment options and poor outcomes, the effect of MEDI4736 on tumors in human patients was examined.

BRIEF SUMMARY

Methods of administering MEDI4736 to human patients and methods of treating tumors in human patients using MEDI4736 are provided herein.

In certain aspects, a method of treating a B7-H1-expressing tumor in a human patient comprises administering MEDI4736 or an antigen-binding fragment thereof to the patient, wherein the administration decreases tumor size.

In certain aspects, a method of minimizing anti-drug antibodies produced by a human patient with a B7-H1-expressing tumor, wherein the patient is being treated with an anti-B7-H1 antibody or antigen-binding fragment thereof, comprises administering MEDI4736 or an antigen-binding fragment thereof to the patient.

In certain aspects, a method of treating a B7-H1-expressing tumor in a human patient comprises administering MEDI4736 or an antigen-binding fragment thereof to the patient, wherein the administration produces an AUC (tau) of about 100 to about 2,500 d·µg/mL.

In certain aspects, a method of treating a B7-H1-expressing tumor in a human patient comprises administering MEDI4736 or an antigen-binding fragment thereof to the patient, wherein the administration produces a Cmax of about 15 to about 350 µg/mL.

In certain aspects, a method of treating a B7-H1-expressing tumor in a human patient comprises administering MEDI4736 or an antigen-binding fragment thereof to the patient, wherein the half-life of the MEDI4736 or the antigen-binding fragment thereof is about 5 to about 25 days.

In certain aspects, a method of treating a B7-H1-expressing tumor in a human patient comprises administering MEDI4736 or an antigen-binding fragment thereof to the patient, wherein the clearance of the MEDI4736 or the antigen-binding fragment thereof is about 1-10 ml/day/kg.

In certain aspects, a method of treating a B7-H1-expressing tumor in a human patient comprises administering to the patient a dose of about 3 mg/kg MEDI4736 or an antigen-binding fragment thereof.

In certain aspects, a method of treating a B7-H1-expressing tumor in a human patient comprises administering to the patient a dose of about 15 mg/kg MEDI4736 or an antigen-binding fragment thereof.

In certain aspects, a method of treating a B7-H1-expressing tumor in a human patient comprises administering MEDI4736 or an antigen-binding fragment thereof, wherein administration of 1 mg/kg of the MEDI4736 or an antigen-binding fragment thereof is sufficient to reduce tumor size.

In some embodiments, at least two doses of the MEDI4736 or the antigen-binding fragment thereof are administered. In some embodiments, at least 3 doses of the MEDI4736 or the antigen-binding fragment thereof are administered. In some embodiments, at least 5 doses of the MEDI4736 or the antigen-binding fragment thereof are administered.

In some embodiments, the administration reduces tumor growth. In some embodiments, the administration decreases tumor size. In some embodiments, the administration decrease tumor size by at least 25%. In some embodiments, the administration decrease tumor size by at least 50%. In some embodiments, the administration decrease tumor size by at least 75%.

In some embodiments, the administration minimizes the likelihood of anti-drug antibodies produced by the patient. In some embodiments, no more than 10% of patients treated with MEDI4736 produce anti-drug antibodies. In some embodiments, no more than 9% of patients treated with MEDI4736 produce anti-drug antibodies. In some embodiments, no more than 8% of patients treated with MEDI4736 produce anti-drug antibodies. In some embodiments, no more than 7% of patients treated with MEDI4736 produce anti-drug antibodies.

In some embodiments, the administration produces a median range of AUC (tau) measurements. Thus, for example, in some embodiments, the administration produces an AUC (tau) of about 100 to about 2,500 d·µg/mL. In some embodiments, the administration produces a median range of Cmax measurements. Thus, for example, in some embodiments, the administration produces a Cmax of about 15 to about 350 µg/mL. In some embodiments, the administration produces a median range of half-life measurements. Thus, for example, in some embodiments, the half-life of the MEDI4736 or the antigen-binding fragment thereof is about 5 to about 25 days. In some embodiments, the administration produces a median range of clearance measurements. Thus, for example, in some embodiments, the clearance of the MEDI4736 or the antigen-binding fragment thereof is about 1-10 ml/day/kg.

In some embodiments, about 0.1, about 0.3, about 1, about 3, about 10, or about 15 mg/kg MEDI4736 or an antigen-binding fragment thereof is administered. In some embodiments, about 1 mg/kg MEDI4736 or an antigen-binding fragment thereof is administered. In some embodiments about 3 mg/kg MEDI4736 or an antigen-binding fragment thereof is administered. In some embodiments, about 10 mg/kg MEDI4736 or an antigen-binding fragment thereof is administered. In some embodiments, about 15 mg/kg MEDI4736 or an antigen-binding fragment thereof is administered.

In some embodiments, the administration is repeated about every 14 to 21 days. In some embodiments, the administration is repeated about every 14 days. In some embodiments, the administration is repeated about every 21 days.

In some embodiments, the tumor size decreases or tumor growth is reduced, and MEDI4736 or an antigen-binding fragment thereof is subsequently administered as a maintenance therapy about every 2 months.

In some embodiments, the tumor size decreases by at least 25% within about 6 weeks. In some embodiments, the administration decrease tumor size by at least 50%. In some embodiments, the tumor size decreases by at least 50% within about 10 weeks. In some embodiments, the administration decrease tumor size by at least 75%. In some embodiments, the tumor size decreases by at least 75% within about 10 weeks.

In some embodiments, the administration results in a partial response. In some embodiments, the administration results in a complete response. In some embodiments, the administration increases progression free survival (PFS). In some embodiments, the administration increases overall survival (OS).

In some embodiments, the administration can reduce free B7-H1 levels by at least 80%. In some embodiments, the administration can reduce free B7-H1 levels by at least 90%. In some embodiments, the administration can reduce free B7-H1 levels by at least 95%. In some embodiments, the administration can reduce free B7-H1 levels by at least 99%. In some embodiments, the administration can reduce the rate of increase in B7-H1 levels.

In some embodiments, the tumor is a solid tumor. In some embodiments, the solid tumor is melanoma, renal cell carcinoma, non-small cell lung cancer, or colorectal cancer. In some embodiments, the tumor is melanoma. In some embodiments, the tumor is renal cell carcinoma. In some embodiments, the tumor is non-small cell lung cancer. In some embodiments, the tumor is colorectal cancer.

In some embodiments, the tumor is NSCLC (Squamous cell carcinoma), hepatocellular cancer (HCC), triple-negative breast cancer (TNBC), pancreatic cancer, GI cancer, melanoma, uveal melanoma, or squamous cell carcinoma of the head and neck (SCCHN). In some embodiments, the tumor is NSCLC (Squamous cell carcinoma). In some embodiments, the tumor is HCC. In some embodiments, the tumor is TNBC. In some embodiments, the tumor is pancreatic cancer. In some embodiments, the tumor is GI cancer.

In some embodiments, the tumor is melanoma. In some embodiments, the tumor is uveal melanoma. In some embodiments, the tumor is SCCHN.

In some embodiments, the tumor is melanoma, renal cell carcinoma, non-small cell lung cancer (squamous cell), non-small cell lung cancer (non-squamous cell), colorectal cancer, HCC, TNBC, pancreatic cancer, GI cancer, uveal melanoma, or SCCHN.

In some embodiments, the tumor is refractory to at least one chemotherapeutic agent. In some embodiments, the chemotherapeutic agent is Vemurafenib, Erlotinib, Afatinib, Cetuximab, Carboplatin, Bevacizumab, Erlotinib, or Pemetrexed.

In some embodiments, the patient has an Eastern Cooperative Oncology Group (ECOG) performance status of 0 or 1.

In some embodiments, the administration is by intravenous infusion. In some embodiments, the administration occurs over about an hour.

In certain aspects of the provided methods, administration of MEDI4736 or an antigen-binding fragment thereof results in the pharmacokinetic profiles as shown in FIGS. 4-6.

In certain aspects of the provided methods, administration of MEDI4736 or an antigen-binding fragment thereof results in in the pharmacokinetic profiles obtained in Example 2.

In certain aspects of the provided methods, administration of MEDI4736 or an antigen-binding fragment thereof results in treatment of a tumor as shown in FIGS. 7-9.

In certain aspects of the provided methods, administration of MEDI4736 or an antigen-binding fragment thereof results in treatment of a tumor as shown in Example 2.

The invention also provides a method of quantifying soluble B7-H1 as shown in Example 3.

In another aspect, the invention provides a method of treating a patient identified as having a B7-H1-expressing tumor, the method involving administering MEDI4736 or an antigen binding fragment thereof to a human patient, where the patient is identified by detecting B7-H1 expression in one or more tumor cells.

In another aspect, the invention provides a method of increasing the efficacy of a MEDI4736 cancer treatment involving administering MEDI4736 to a human patient identified as having tumor cells expressing B7-H1.

In various embodiments of the previous aspects, B7-H1 is detected using immunohistochemistry, for example, in formalin fixed and paraffin embedded tumor samples. In other embodiments, at least 25% of the tumor cells contain B7-H1-membrane staining. In other embodiments, there is a 40% or 50% objective response rate in patients identified as having a B7-H1-expressing tumor. In other embodiments, the tumor is a melanoma, renal cell carcinoma, non-small cell lung cancer, pancreatic adenocarcinoma, gastroesophageal carcinoma, uveal melanoma, triple negative breast carcinoma, hepatocellular carcinoma, squamous cell carcinoma, or colorectal cancer. In other embodiments, the tumor is a non-small cell lung cancer (e.g., squamous cell carcinoma or a non-squamous cell carcinoma). In other embodiments, the tumor is a squamous cell carcinoma of the head and neck. In other embodiments, about 0.1, about 0.3, about 1, about 3, about 10, or about 15 mg/kg MEDI4736 or an antigen-binding fragment thereof is administered. In particular embodiments, the administration is repeated about ever 14 or 21 days. In other embodiments, at least two, three, four, or five doses of MEDI4736 is administered.

BRIEF DESCRIPTION OF THE DRAWINGS/FIGURES

FIG. 1 shows the timeline of treatment with MEDI4736 administered intravenously (IV) every two weeks (Q2W).

Immune-related response criteria (irRC) are measured after weeks 6, 12, and 16 and then every 8 weeks.

FIG. 2A shows the study flow diagram for the dose-expansion and dose-escalation portions of the study. The dose expansion portion of the study is conducted using a two-week dosing schedule (Q2W) and a three-week dosing schedule (Q3W). Patients with non-small cell lung cancer (NSCLC), melanoma, and other tumors are evaluated in the escalation portion of the study.

FIG. 3 shows the baseline demographics of subjects treated with 0.1, 0.3, 1, 3, 10, or 15 mg/kg of MED4736 in the dose-escalation study.

FIG. 4 shows a summary of the pharmacokinetic data obtained after administering MEDI4736 (Q2W) at 0.1 mg/kg or 0.3 mg/kg during the dose-escalation phase of the study. "AUC"=area under the curve; "Cmax"=maximum observed concentration (Panel A).

FIG. 7 shows the clinical activity of MEDI4736 observed in patients with non-small cell lung cancer (NSCLC), melanoma, or colorectal cancer (CRC) receiving 0.1 mg/kg, 0.3 mg/kg, or 1 mg/kg MEDI4736. Best responses are characterized as stable disease (SD), progressive disease (PD), partial response (PR), or not evaluable (NE)

FIG. 13 shows the percent change of tumor size from baseline for pancreatic adenocarcinoma patients treated with 10 mg/kg MEDI4736 2QW (Panel A); The best change in tumor size from baseline is shown in Panel B.

FIGS. 14A&B shows the percent change of tumor size from baseline for gastroesophageal cancer patients treated with 10 mg/kg MEDI4736 2QW (FIG. 14A). The best change in tumor size from baseline is shown in FIG. 14B.

Figure 15:
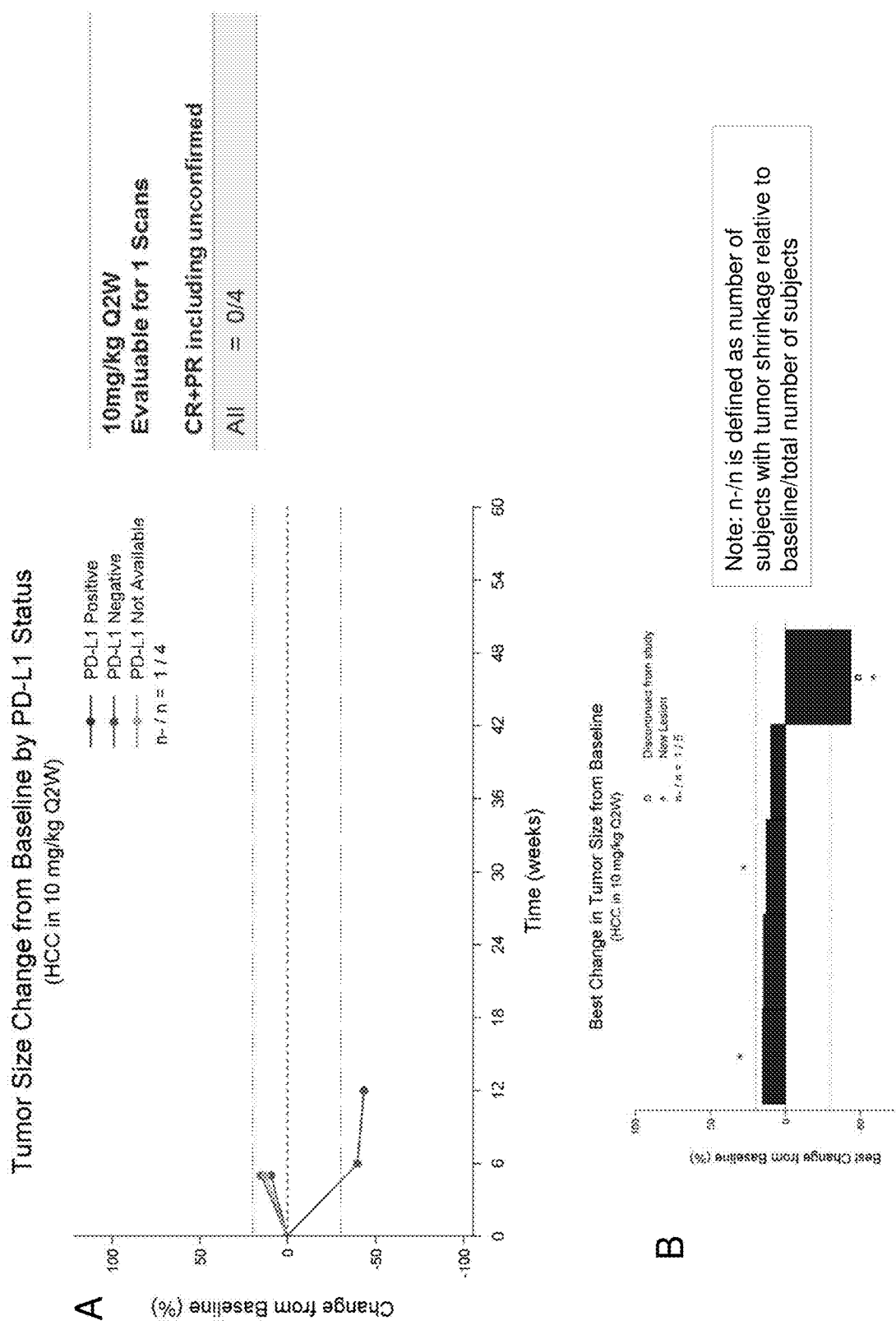

FIG. 15 shows the percent change of tumor size from baseline for hepatocellular carcinoma (HCC) patients treated with 10 mg/kg MEDI4736 2QW. The best change in tumor size from baseline is shown in Panel B.

Figure 16:
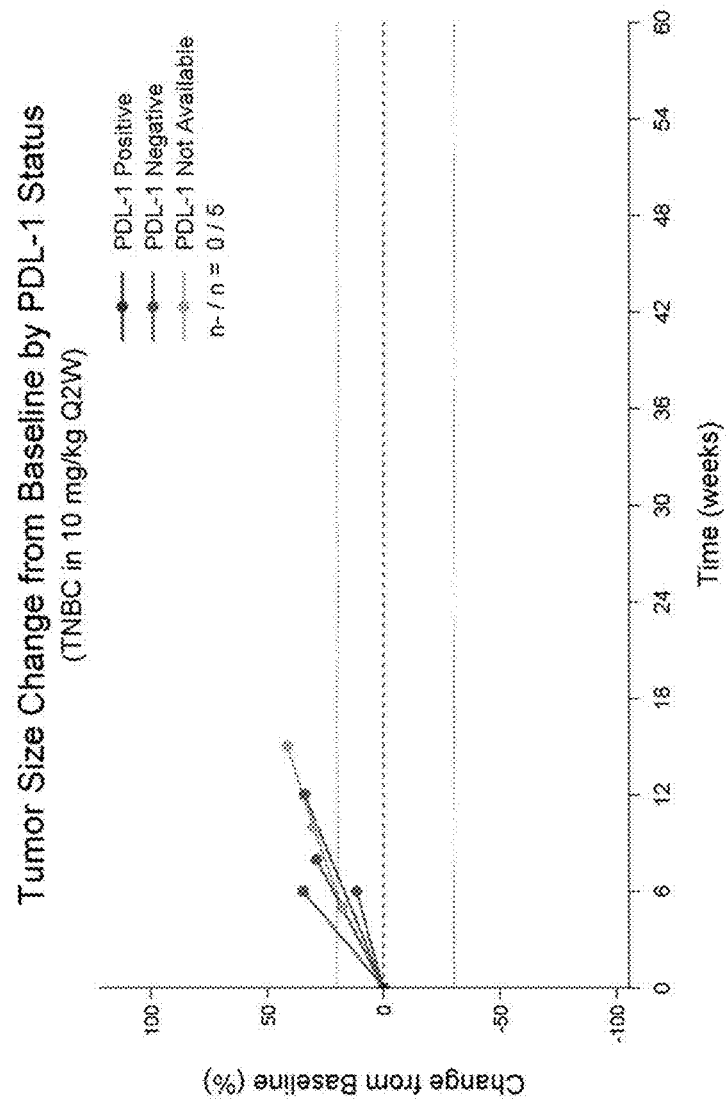

FIG. 16 shows the percent change of tumor size from baseline for triple negative breast cancer (TNBC) patients treated with 10 mg/kg MEDI4736 2QW.

Figure 17:
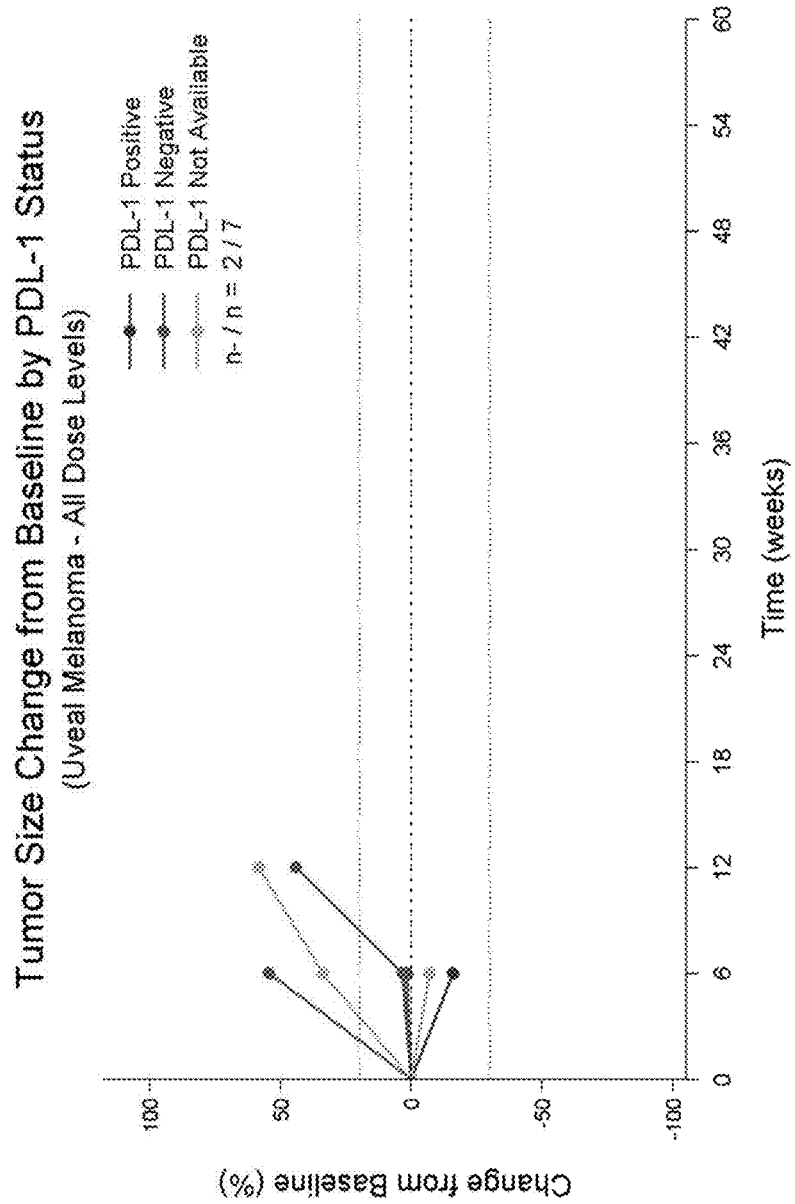

FIG. 17 shows the percent change of tumor size from baseline for uveal melanoma patients treated with 10 mg/kg MEDI4736 2QW.

Figure 18A:
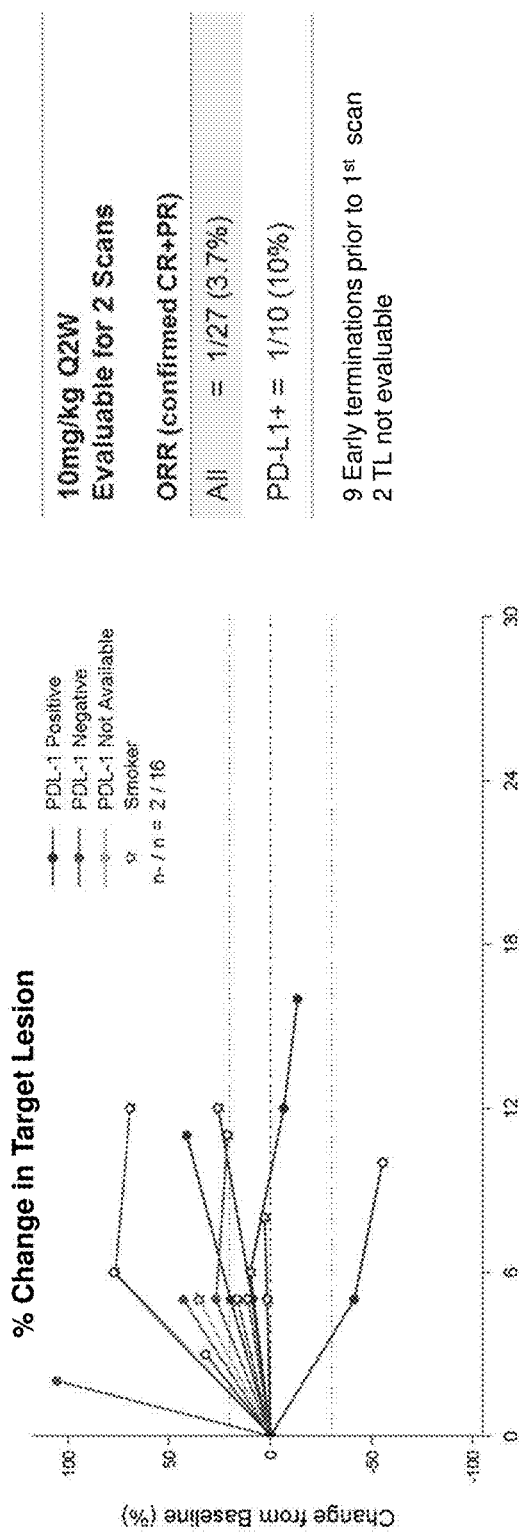

FIG. 18A shows a comparison of the percent change in tumor size from baseline for NSCLC patients treated with 10 mg/kg MEDI4736 2QW evaluable for 2 scans. The plot shows patients with PD-L1 Positive tumors, PD-L1 Negative tumors and patients whose PD-L1 tumor status was not available. Patients that were identified as smokers are shown with a star. The ORR (confirmed CR+PR) for all patients was 3.7%. The ORR rate for PD-L1+patients was 10%.

Figure 18B:
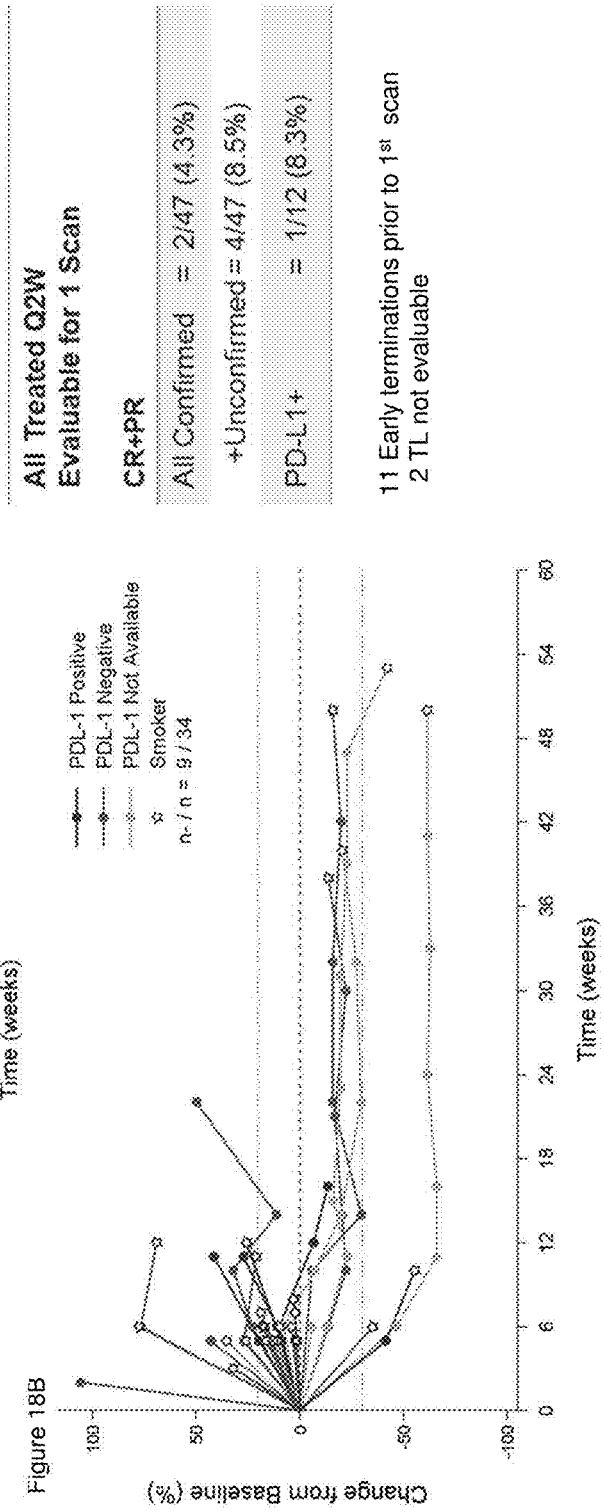

FIG. 18B shows a comparison of the percent change in tumor size from baseline for NSCLC patients treated with all dose levels of MEDI4736 2QW evaluable for 1 scan. The plot shows patients with PD-L1 Positive tumors, PD-L1 Negative tumors and patients whose PD-L1 tumor status was not available. Patients that were identified as smokers are shown with a star. The ORR (confirmed CR+PR) for all confirmed patients was 4.3% (ORR for all unconfirmed patients was 8.5%). The ORR rate for PD-L1+patients was 8.3%.

Figure 19:
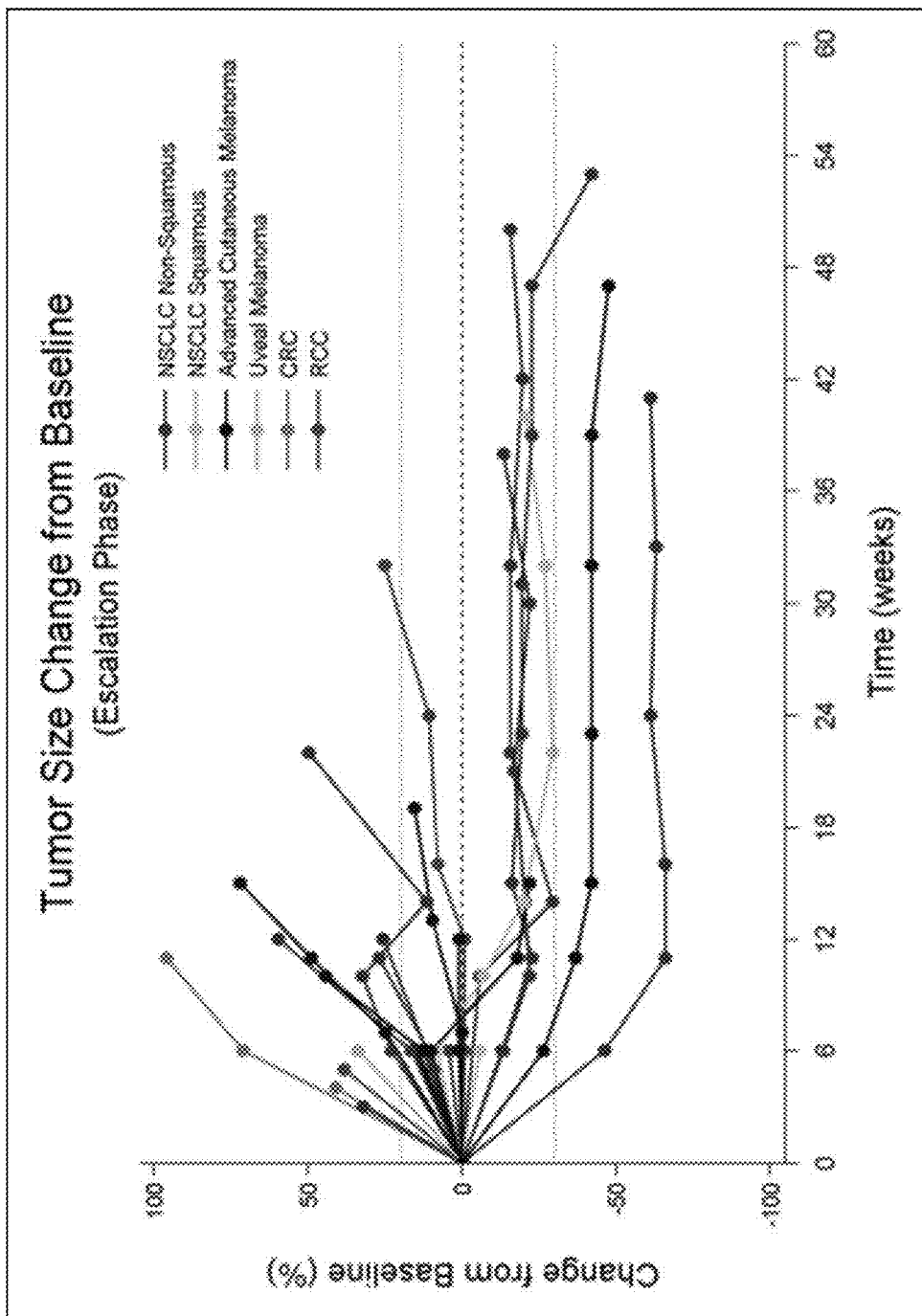

FIG. 19 shows the change in tumor size for 6 tumor types in the Escalation Phase.

Figure 20:
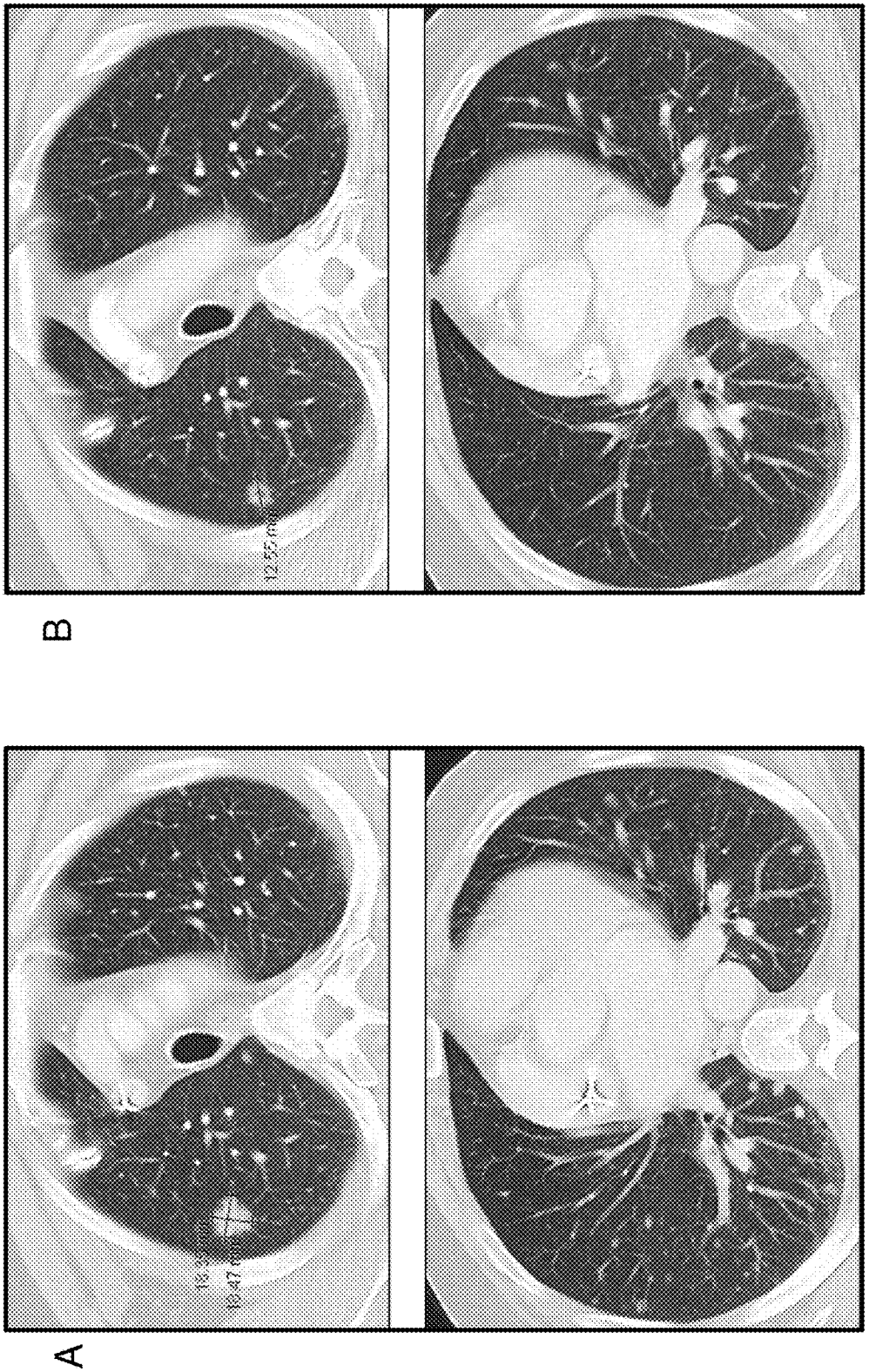

FIG. 20 shows the response of a pancreatic cancer patient treated with 10 mg/kg Q2W MEDI4736. Panel A shows the initial screening and Panel B shows the subject at week 6.

Figure 21:
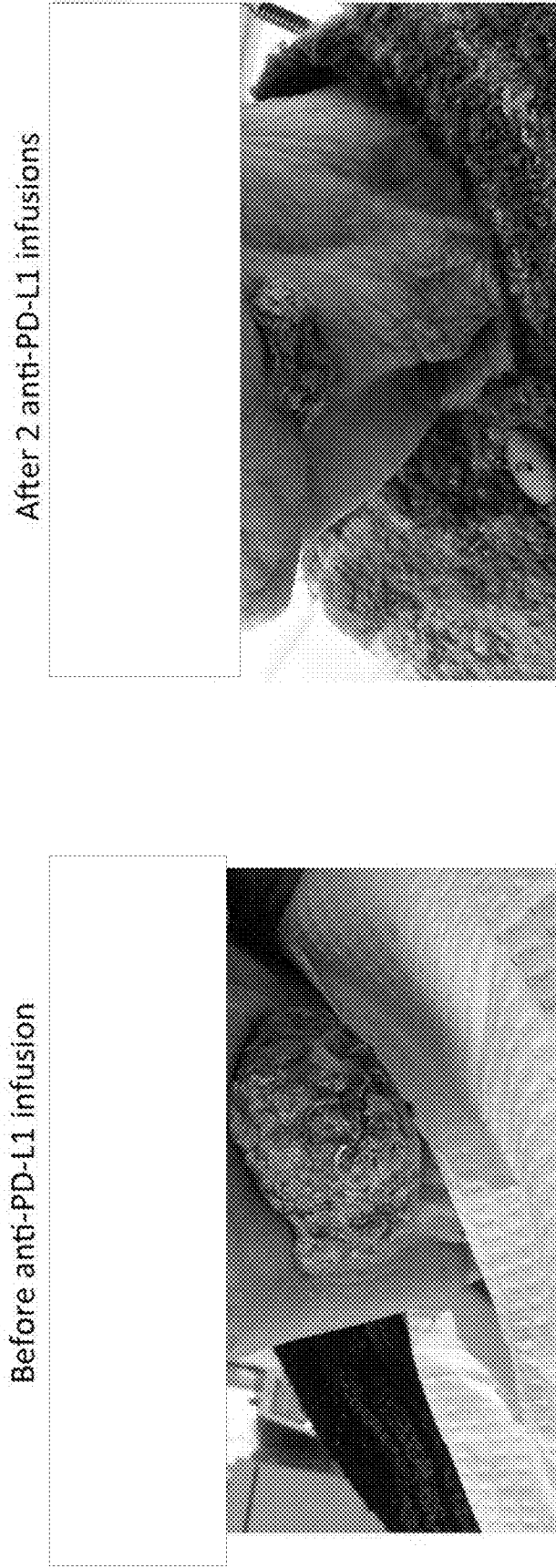

FIG. 21 shows response in a female patient with SCCHN before (Panel A) and after (Panel B) treatment with 2 infusions of 10 mg/kg MEDI4736.

Figure 22:
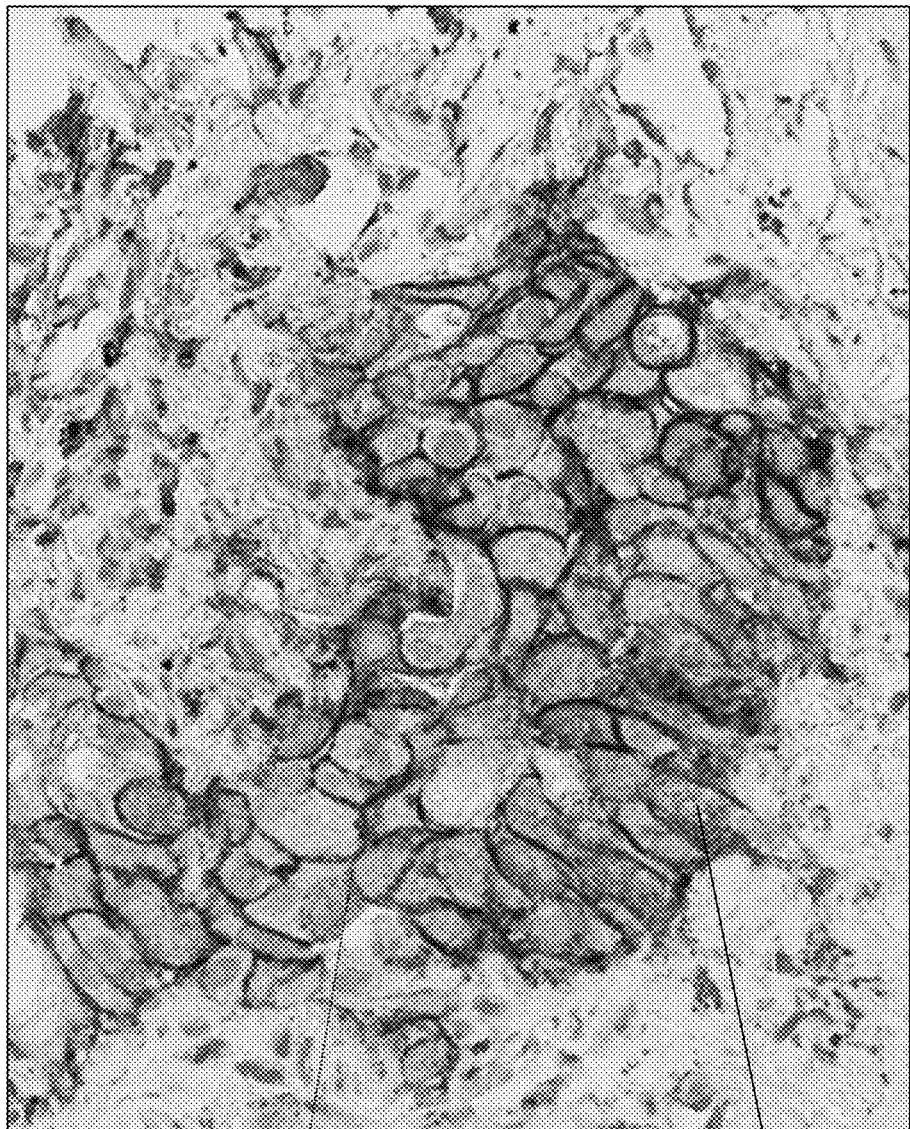

FIG. 22 shows staining of PD-L1 in Subject tissue of NSCLC (fresh biopsy).

Figure 23:
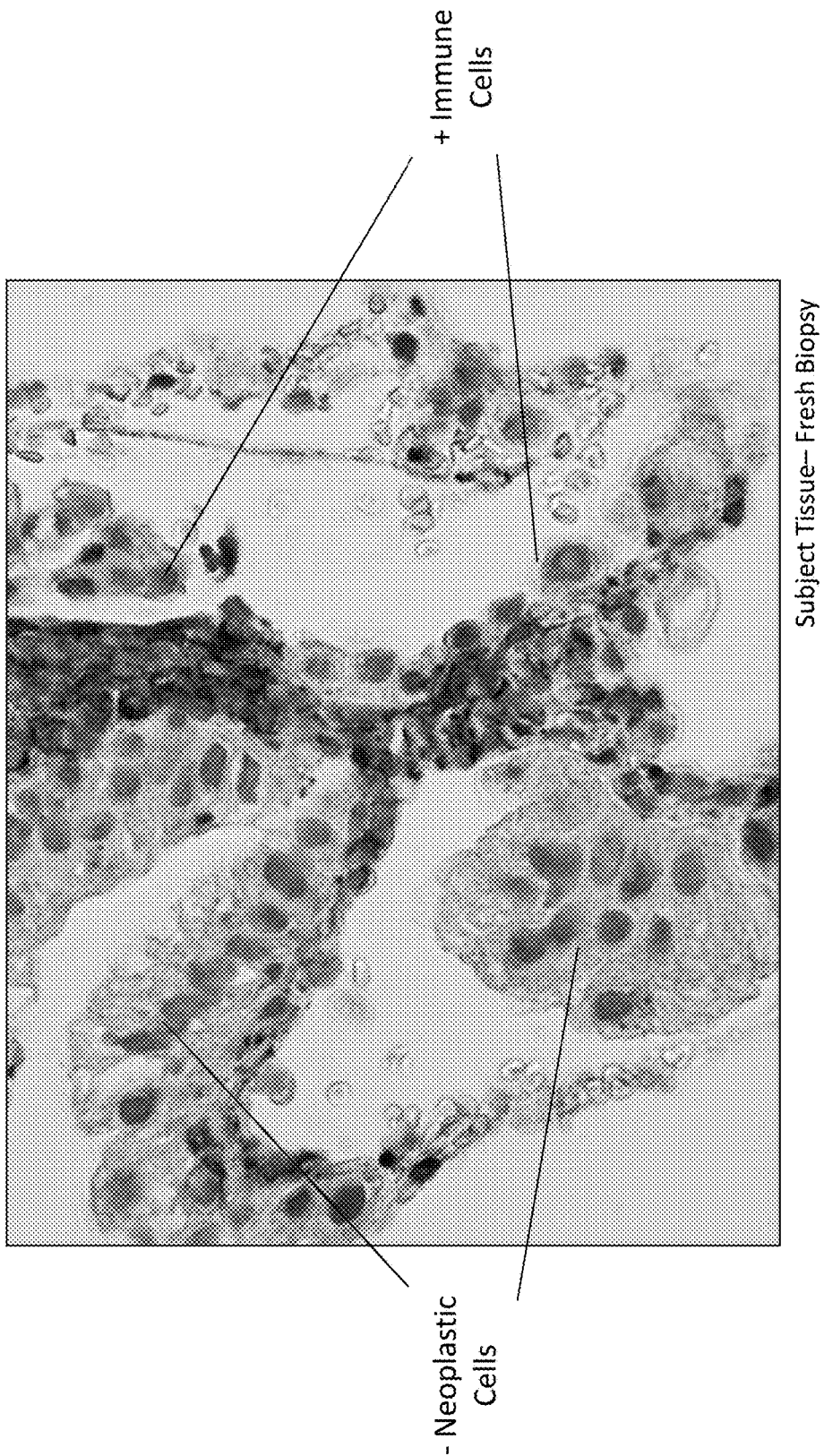

FIG. 23 shows staining of PD-L1 in Subject tissue (fresh biopsy) indicating neoplastic cells and immune cells.

Figure 24:
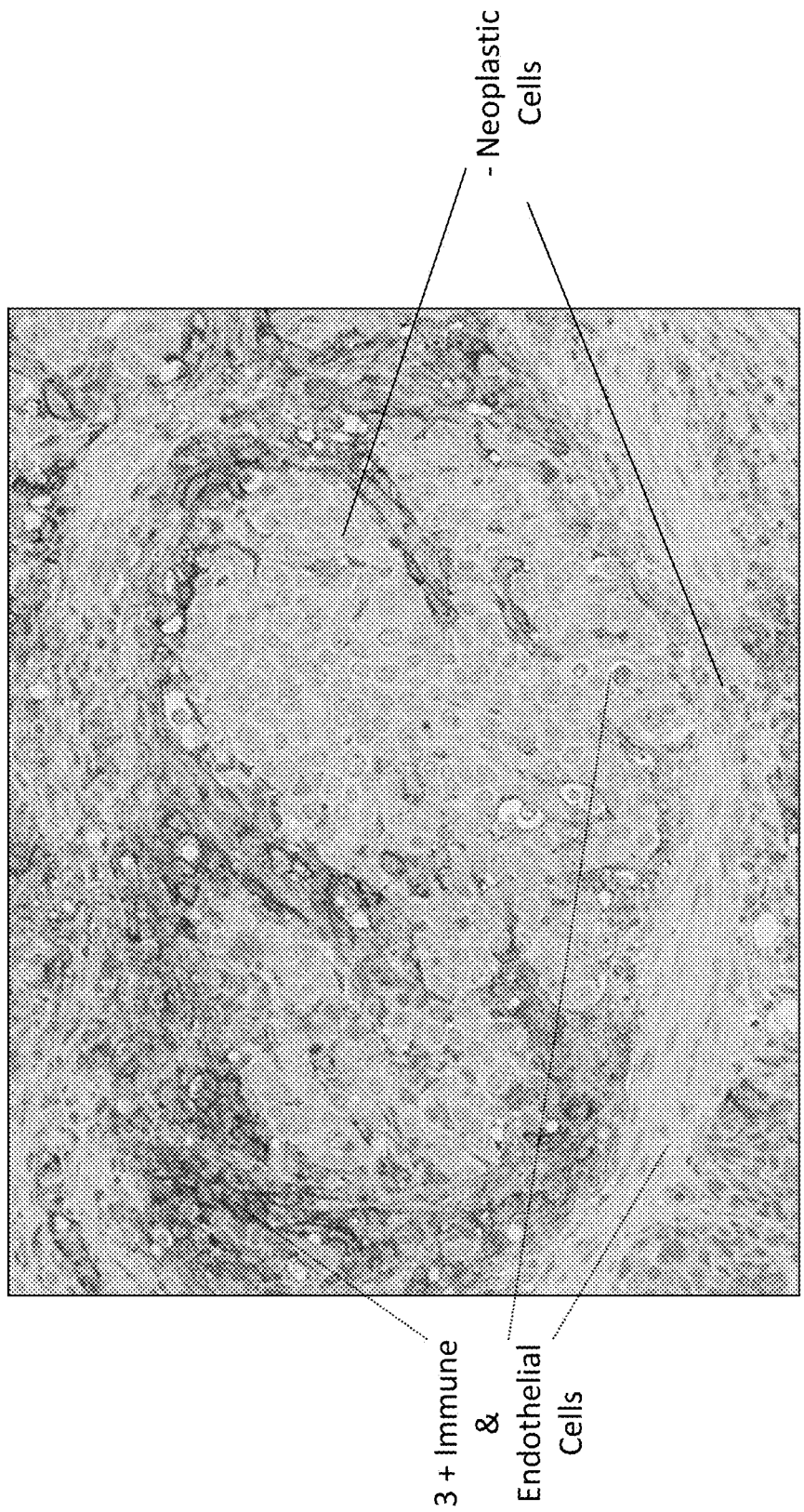

FIG. 24 shows staining of PD-L1 in Subject tissue) indicating neoplastic cells and immune and endothelial cells.

Figure 25A:
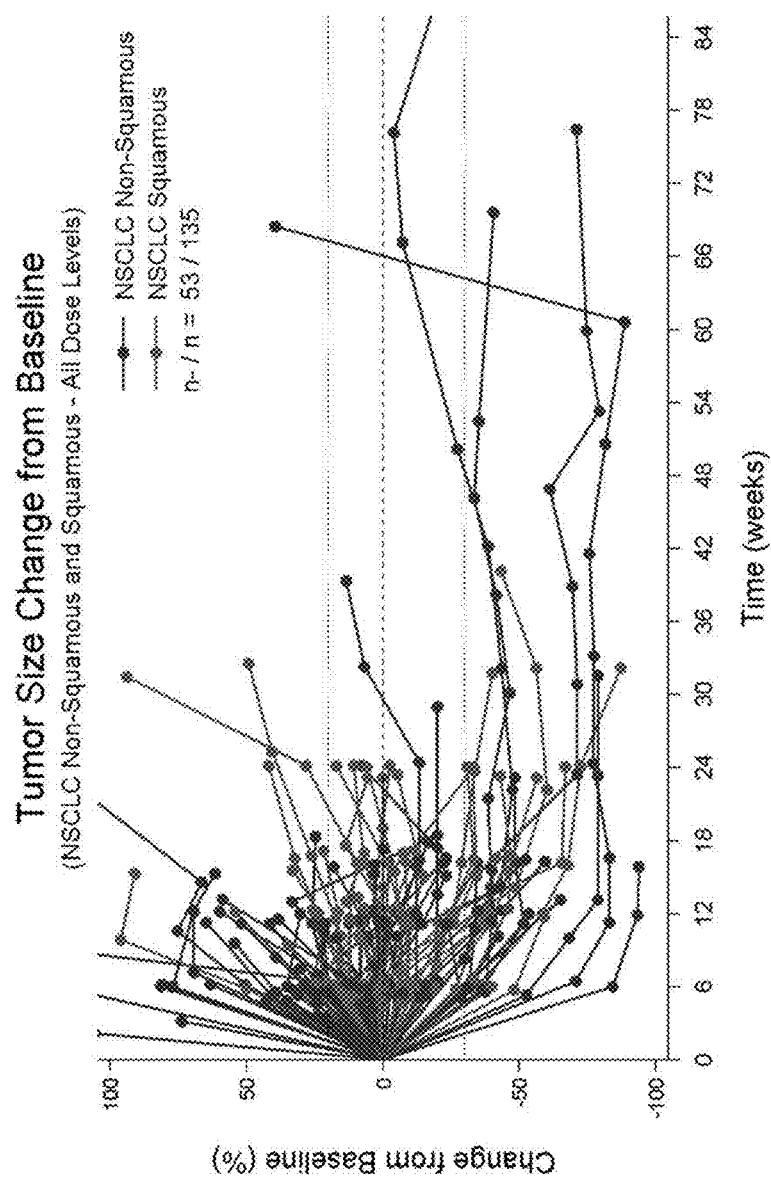
Figure 25B:
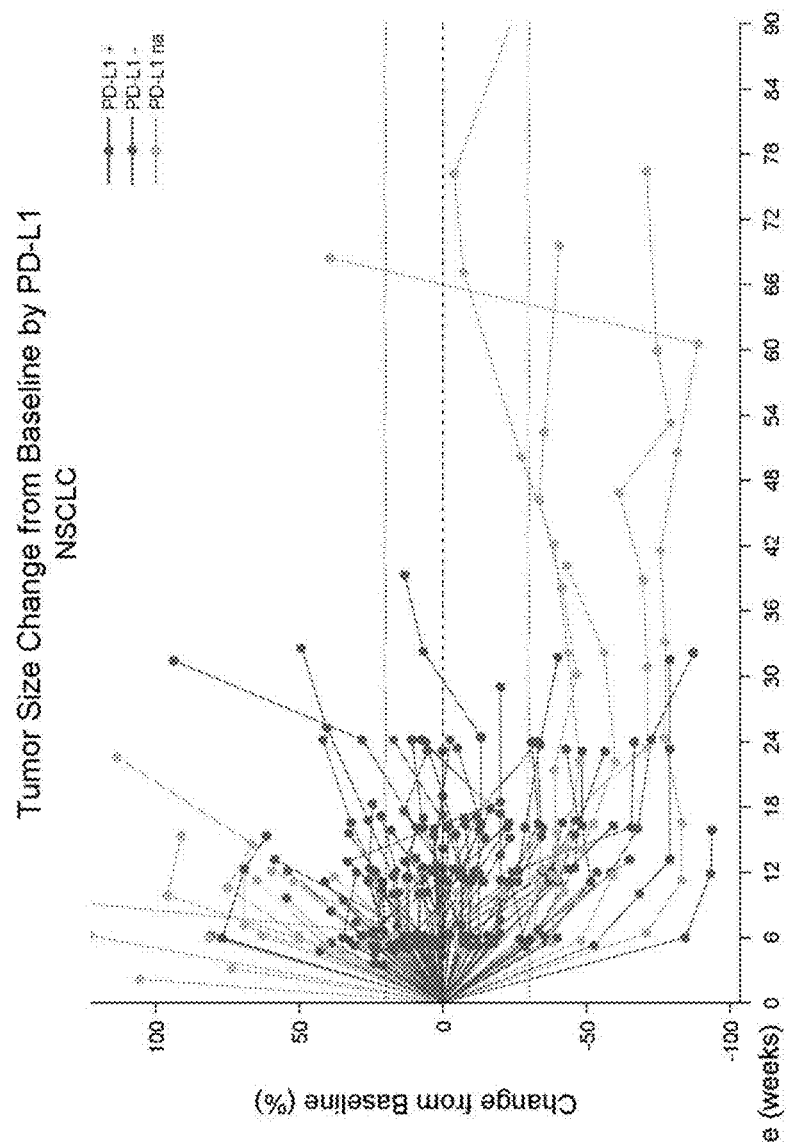
Figure 25C:
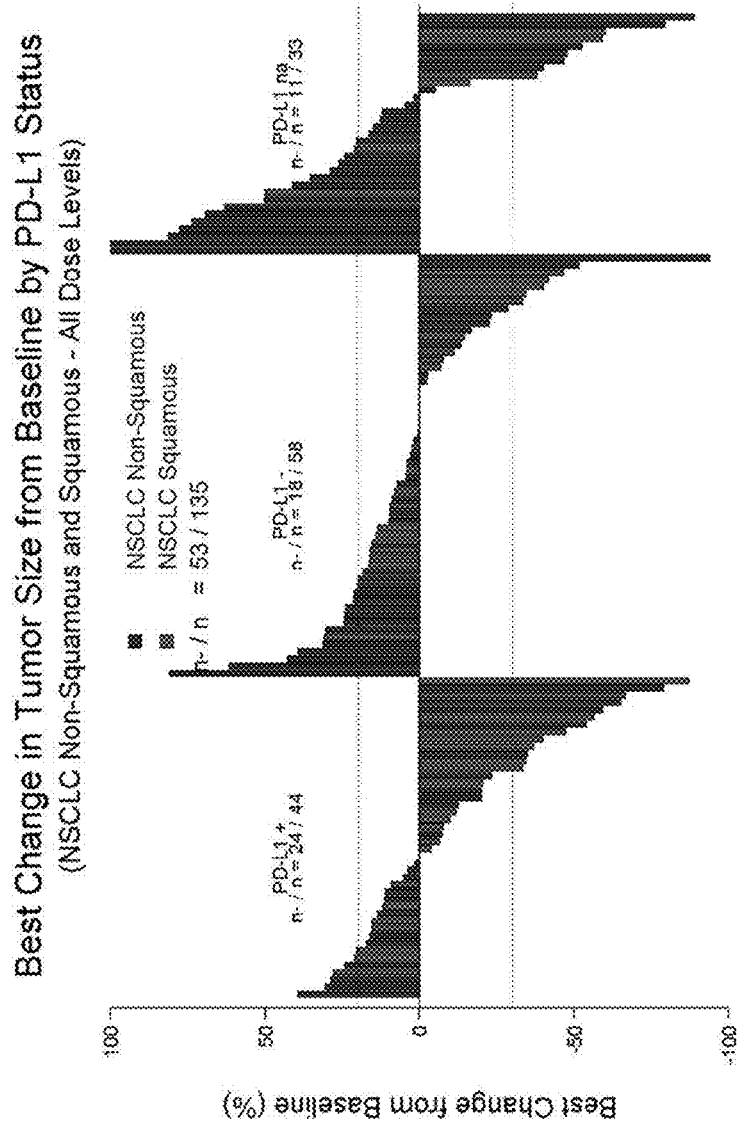

FIGS. 25A-C show the response in the patients to treatment of MEDI4736 relative to their PD-L1 tumor status. FIG. 25A is a spider plot showing tumor size following MEDI4736 treatment in Non-squamous and Squamous NSCLC. FIG. 25B is a spider plot showing tumor size following MEDI4736 treatment in PD-L1 positive and PD-L1 negative NSCLC tumors. FIG. 25C is a waterfall plot showing change in tumor size in PD-L1 positive and PD-L1 negative NSCLC patients.

DETAILED DESCRIPTION

It is to be noted that the term "a" or "an" entity refers to one or more of that entity; for example, "an anti-B7-H1 antibody" is understood to represent one or more anti-B7-H1 antibodies. As such, the terms "a" (or "an"), "one or more," and "at least one" can be used interchangeably herein.

Provided herein are methods for treating tumors. The methods provided include administering an effective amount of MEDI4736 or an antigen-binding fragment thereof.

Information regarding MEDI4736 (or fragments thereof) for use in the methods provided herein can be found in International Application Publication No. WO 2011/066389 A1, the disclosure of which is incorporated herein by reference in its entirety. The fragment crystallizable (Fc) domain of MEDI4736 contains a triple mutation in the constant domain of the IgG1 heavy chain that reduces binding to the complement component C1q and the Fcγ receptors responsible for mediating antibody-dependent cell-mediated cytotoxicity (ADCC). MEDI4736 is selective for B7-H1 and blocks the binding of B7-H1 to the PD-1 and CD80 receptors. MEDI4736 can relieve B7-H1-mediated suppression of human T-cell activation in vitro and inhibits tumor growth in a xenograft model via a T-cell dependent mechanism.

MEDI4736 and antigen-binding fragments thereof for use in the methods provided herein comprises a heavy chain and a light chain or a heavy chain variable region and a light chain variable region. In a specific aspect, MEDI4736 or an antigen-binding fragment thereof for use in the methods provided herein comprises a light chain variable region comprising the amino acid sequence of SEQ ID NO:1 and a heavy chain variable region comprising the amino acid sequence of SEQ ID NO:2. In a specific aspect, MEDI4736 or an antigen-binding fragment thereof for use in the methods provided herein comprises a heavy chain variable region and a light chain variable region, wherein the heavy chain variable region comprises the Kabat-defined CDR1, CDR2, and CDR3 sequences of SEQ ID NOs:3-5, and wherein the light chain variable region comprises the Kabat-defined CDR1, CDR2, and CDR3 sequences of SEQ ID NOs:6-8. Those of ordinary skill in the art would easily be able to identify Chothia-defined, Abm-defined or other CDR definitions known to those of ordinary skill in the art. In a specific aspect, MEDI4736 or an antigen-binding fragment thereof for use in the methods provided herein comprises the variable heavy chain and variable light chain CDR sequences of the 2.14H9OPT antibody as disclosed in WO 2011/066389 A1, which is herein incorporated by reference in its entirety.

In certain aspects, a patient presenting with a tumor is administered MEDI4736 or an antigen-binding fragment thereof. MEDI4736 or an antigen-binding fragment thereof can be administered only once or infrequently while still providing benefit to the patient. In further aspects the patient is administered additional follow-on doses. Follow-on doses can be administered at various time intervals depending on the patient's age, weight, clinical assessment, tumor burden, and/or other factors, including the judgment of the attending physician.

The intervals between doses can be every two weeks. The interval between doses can be every three weeks. The intervals between doses can be every two months (e.g., during a maintenance phase).

The dosing intervals can also be about every 14 days or about every 21 days. In some embodiments, "about" every 14 days or "about" every 21 days indicates 14 days+/−2 days or 21 days+/−2 days. In some embodiments, administration of MEDI4736 is about every 14 to 21 days.

In some embodiments, at least two doses of MEDI4736 or an antigen-binding fragment thereof are administered to the patient. In some embodiments, at least three doses, at least four doses, at least five doses, at least six doses, at least seven doses, at least eight doses, at least nine doses, at least ten doses, or at least fifteen doses or more can be administered to the patient. In some embodiments, MEDI4736 or an antigen-binding fragment thereof is administered over a two-week treatment period, over a four-week treatment period, over a six-week treatment period, over an eight-week treatment period, over a twelve-week treatment period, over a twenty-four-week treatment period, or over a one-year or more treatment period. In some embodiments, MEDI4736 or an antigen-binding fragment thereof is administered over a three-week treatment period, a six-week treatment period, over a nine-week treatment period, over a twelve-week treatment period, over a twenty-four-week treatment period, or over a one-year or more treatment period. In some embodiments, MEDI4736 or an antigen-binding fragment thereof is administered over a two-month treatment period, over a four-month treatment period, or over a six-month or more treatment period (e.g., during a maintenance phase).

The amount of MEDI4736 or an antigen-binding fragment thereof to be administered to the patient will depend on various parameters such as the patient's age, weight, clinical assessment, tumor burden and/or other factors, including the judgment of the attending physician.

In certain aspects the patient is administered one or more doses of MEDI4736 or an antigen-binding fragment thereof wherein the dose is about 0.1 mg/kg. In certain aspects the patient is administered one or more doses of MEDI4736 or an antigen-binding fragment thereof wherein the dose is about 0.3 mg/kg. In certain aspects the patient is administered one or more doses of MEDI4736 or an antigen-binding fragment thereof wherein the dose is about 1 mg/kg. In certain aspects the patient is administered one or more doses of MEDI4736 or an antigen-binding fragment thereof wherein the dose is about 3 mg/kg. In certain aspects the patient is administered one or more doses of MEDI4736 or an antigen-binding fragment thereof wherein the dose is about 10 mg/kg. In certain aspects the patient is administered one or more doses of MEDI4736 or an antigen-binding fragment thereof wherein the dose is about 15 mg/kg.

In certain aspects the patient is administered at least two doses of MEDI4736 or an antigen-binding fragment thereof wherein the dose is about 0.1 mg/kg. In certain aspects the patient is administered at least two doses of MEDI4736 or an antigen-binding fragment thereof wherein the dose is about 0.3 mg/kg. In certain aspects the patient is administered at least two doses of MEDI4736 or an antigen-binding fragment thereof wherein the dose is about 1 mg/kg. In certain aspects the patient is administered at least two doses of MEDI4736 or an antigen-binding fragment thereof wherein the dose is about 3 mg/kg. In certain aspects the patient is administered at least two doses of MEDI4736 or an antigen-binding fragment thereof wherein the dose is about 10 mg/kg. In certain aspects the patient is administered at least two doses of MEDI4736 or an antigen-binding fragment thereof wherein the dose is about 15 mg/kg. In some embodiments, the at least two doses are administered about two weeks apart. In some embodiments, the at least two doses are administered about three weeks apart.

In certain aspects the patient is administered at least three doses of MEDI4736 or an antigen-binding fragment thereof wherein the dose is about 0.1 mg/kg. In certain aspects the patient is administered at least three doses of MEDI4736 or an antigen-binding fragment thereof wherein the dose is about 0.3 mg/kg. In certain aspects the patient is administered at least three doses of MEDI4736 or an antigen-binding fragment thereof wherein the dose is about 1 mg/kg. In certain aspects the patient is administered at least three doses of MEDI4736 or an antigen-binding fragment thereof wherein the dose is about 3 mg/kg. In certain aspects the patient is administered at least three doses of MEDI4736 or an antigen-binding fragment thereof wherein the dose is about 10 mg/kg. In certain aspects the patient is administered at least three doses of MEDI4736 or an antigen-binding fragment thereof wherein the dose is about 15 mg/kg. In some embodiments, the at least three doses are administered about two weeks apart. In some embodiment, the at least three doses are administered about three weeks apart.

In certain aspects, administration of MEDI4736 or an antigen-binding fragment thereof according to the methods provided herein is through parenteral administration. For example, MEDI4736 or an antigen-binding fragment thereof can be administered by intravenous infusion or by subcutaneous injection. In some embodiments, the administration is by intravenous infusion.

In certain aspects, MEDI4736 or an antigen-binding fragment thereof is administered according to the methods provided herein in combination or in conjunction with additional cancer therapies. Such therapies include, without limitation, chemotherapeutic agents such as Vemurafenib, Erlotinib, Afatinib, Cetuximab, Carboplatin, Bevacizumab, Erlotinib, or Pemetrexed, or other chemotherapeutic agents, as well radiation or any other anti-cancer treatments.

The methods provided herein can decrease tumor size, retard tumor growth or maintain a steady state. In certain aspects the reduction in tumor size can be significant based on appropriate statistical analyses. A reduction in tumor size can be measured by comparison to the size of patient's tumor at baseline, against an expected tumor size, against an expected tumor size based on a large patient population, or against the tumor size of a control population. In certain aspects provided herein, the administration of MEDI4736 can reduce a tumor size by at least 25%. In certain aspects provided herein, the administration of MEDI4736 can reduce a tumor size by at least 25% within about 6 weeks of the first treatment. In certain aspects provided herein, the administration of MEDI4736 can reduce a tumor size by at least 50%. In certain aspects provided herein, the administration of MEDI4736 can reduce a tumor size by at least 50% within about 10 weeks of the first treatment. In certain aspects provided herein, the administration of MEDI4736 can reduce a tumor size by at least 75%. In certain aspects provided herein, the administration of MEDI4736 can reduce a tumor size by at least 75% within about 10 weeks of the first treatment.

In certain aspects, use of the methods provided herein, i.e., administration of MEDI4736 or an antigen-binding fragment thereof can decrease tumor size within 6 weeks, within 7 weeks, within 8 weeks, within 9 weeks, within 10 weeks, within 12 weeks, within 16 weeks, within 20 weeks, within 24 weeks, within 28 weeks, within 32 weeks, within 36 weeks, within 40 weeks, within 44 weeks, within 48 weeks, or within 52 weeks of the first treatment.

In some embodiments, administration of 1 mg/kg of MEDI4736 or an antigen-binding fragment thereof (e.g., at least one dose, at least two doses, at least three doses, at least four doses, at least five doses, at least six doses, at least seven doses, at least eight doses, at least nine doses, at least ten doses, or more every two weeks or every three weeks) can be sufficient to reduce tumor size. However, as provided herein, larger doses can also be administered, for example, to optimize efficacy, number of doses necessary, or certain pharmacokinetic parameters.

The methods provided herein can decrease or retard tumor growth. In some aspects the reduction or retardation can be statistically significant. A reduction in tumor growth can be measured by comparison to the growth of patient's tumor at baseline, against an expected tumor growth, against an expected tumor growth based on a large patient population, or against the tumor growth of a control population.

In certain aspects, a patient achieves disease control (DC). Disease control can be a complete response (CR), partial response (PR), or stable disease (SD).

A "complete response" (CR) refers to the disappearance of all lesions, whether measurable or not, and no new lesions. Confirmation can be obtained using a repeat, consecutive assessment no less than four weeks from the date of first documentation. New, non-measurable lesions preclude CR.

A "partial response" (PR) refers to a decrease in tumor burden≥50% relative to baseline. Confirmation can be obtained using a consecutive repeat assessment at least 4 weeks from the date of first documentation "Progressive disease" (PD) refers to an increase in tumor burden≥25% relative to the minimum recorded (nadir). Confirmation can be obtained by a consecutive repeat assessment at least 4 weeks from the date of first documentation. New, non-measurable lesions do not define PD.

"Stable disease" (SD) refers to not meeting the criteria for CR, PR, or PD.

In certain aspects, administration of MEDI4736 or an antigen-binding fragment thereof can increase progression-free survival (PFS).

In certain aspects, administration of MEDI4736 or an antigen-binding fragment thereof can increase overall survival (OS).

In certain aspects, the patient has a particular type of tumor. In some embodiments, the tumor is a solid tumor. In some embodiments, the tumor is a melanoma, a renal cell carcinoma, a non-small cell lung cancer (e.g., squamous or adenocarcinoma), or a colorectal cancer. In some embodiments, the tumor is a melanoma, a non-small cell lung cancer (e.g., squamous or adenocarcinoma), or a colorectal cancer. In some embodiments, the tumor is melanoma. In some embodiments, the tumor is renal cell carcinoma. In some embodiments, the tumor is non-small cell lung cancer. In some embodiments, the tumor is colorectal cancer.

In some embodiments, the tumor is NSCLC (Squamous cell carcinoma), hepatocellular cancer (HCC), triple-negative breast cancer (TNBC), pancreatic cancer, GI cancer, melanoma, uveal melanoma, or squamous cell carcinoma of the head and neck (SCCHN). In some embodiments, the tumor is NSCLC (Squamous cell carcinoma). In some embodiments, the tumor is HCC. In some embodiments, the tumor is TNBC. In some embodiments, the tumor is pancreatic cancer. In some embodiments, the tumor is GI cancer. In some embodiments, the tumor is melanoma. In some embodiments, the tumor is uveal melanoma. In some embodiments, the tumor is SCCHN.

In some embodiments, the tumor is melanoma, renal cell carcinoma, non-small cell lung cancer (squamous cell), non-small cell lung cancer (non-squamous cell), colorectal cancer, HCC, TNBC, pancreatic cancer, GI cancer, uveal melanoma, or SCCHN.

In some embodiments, the patient has previously received treatment with at least one chemotherapeutic agent. In some embodiments, the patient has previously received treatment with at least two chemotherapeutic agents. The chemotherapeutic agent can be, for example, and without limitation, Vemurafenib, Erlotinib, Afatinib, Cetuximab, Carboplatin, Bevacizumab, Erlotinib, and/or Pemetrexed.

In some embodiments, the tumor is refractory or resistant to at least one chemotherapeutic agent. In some embodiments, the tumor is refractory or resistant to at least two chemotherapeutic agents. The tumor can be refractory or resistant to one or more of, for example, and without limitation, Vemurafenib, Erlotinib, Afatinib, Cetuximab, Carboplatin, Bevacizumab, Erlotinib, and/or Pemetrexed.

In some embodiments, the patient has an Eastern Cooperative Oncology Group (ECOG) (Oken M M, et al. *Am. J. Clin. Oncol.* 5: 649-55 (1982)) performance status of 0 or 1 prior to the administration of MEDI4736 or an antigen-binding fragment thereof.

According to the methods provided herein, administration of MEDI4736 or an antigen-binding fragment thereof can result in desirable pharmacokinetic parameters. Total drug exposure can be estimated using the "area under the curve" (AUC). "AUC (tau)" refers to AUC until the end of the dosing period, whereas "AUC (inf)" refers to the AUC until infinite time. The administration can produce AUC (tau) of about 100 to about 2,500 d·µg/mL. The administration can produce a maximum observed concentration (Cmax) of about 15 to about 350 µg/mL. The half-life of the MEDI4736 or the antigen-binding fragment thereof can be about 5 to about 25 days. In addition, the clearance of the MEDI4736 or the antigen-binding fragment thereof can be about 1-10 ml/day/kg.

As provided herein, MEDI4736 or an antigen-binding fragment thereof can also decrease free B7-H1 levels. Free B7-H1 refers to B7-H1 that is not bound (e.g., by MEDI4736). In some embodiments, B7-H1 levels are reduced by at least 80%. In some embodiments, B7-H1 levels are reduced by at least 90%. In some embodiments, B7-H1 levels are reduced by at least 95%. In some embodiments, B7-H1 levels are reduced by at least 99%. In some embodiments, B7-H1 levels are eliminated following administration of MEDI4736 or an antigen-binding fragment thereof. In some embodiments, administration of MEDI4736 or an antigen-binding fragment thereof reduces the rate of increase of B7-H1 levels as compared, e.g., to the rate of increase of B7-H1 levels prior to the administration of MEDI4736 or an antigen-binding fragment thereof.

Advantageously, the methods of administration provided herein also minimize anti-drug antibody responses provided herein. Accordingly, in some embodiments, administration of MEDI4736 or an antigen-binding fragment thereof to a patient in need of treatment with an anti-B7-H1, anti-B7-1, or anti-PD-1, minimizes the anti-drug antibodies produced by the patient. In some embodiments, anti-drug antibodies do not impact MEDI4736 exposure in patients treated with MEDI4736.

EXAMPLES

Example 1: Patients and Methods (a) Subjects

Subjects in this study were required to be 18 years of age or older with advanced malignant melanoma, renal cell carcinoma (RCC), non-small cell lung cancer (NSCLC), or colorectal cancer (CRC) refractory to standard therapy or for which no standard therapy exists. Subjects in the dose-expansion phase of the study will be adults with advanced malignant melanoma, NSCLC, or CRC refractory to standard therapy or for which no standard therapy exists. Additional subjects in the dose-expansion phase had NSCLC (Squamous cell carcinoma), hepatocellular cancer (HCC), triple-negative breast cancer (TNBC), pancreatic cancer, GI cancer, melanoma, uveal melanoma, or Squamous cell carcinoma of the head and neck (SCCHN). The cancers must be histologically- or cytologically confirmed. The subjects are required to have an Eastern Cooperative Oncology Group (ECOG) status of 0 or 1 as well as adequate organ and marrow function. Adequate organ and marrow function was defined as: hemoglobin≥9 g/dL; absolute neutrophil count≥1,500/mm³; lymphocyte count≥800/mm³; platelet count≥100,000/mm³; aspartate aminotransferase (AST) and alanine aminotransferase (ALT)<2.5×institutional upper limit of normal (ULN); bilirubin≤1.5×ULN except in the case of subjects with documented or suspected Gilbert's disease (for these subjects, bilirubin must be ≤5×ULN); creatinine clearance≥50 mL/min as determined by the Cockcroft-Gault equation or by 24-hour urine collection for determination of creatinine clearance.

Subjects are not able to participate if they have active autoimmune disease, prior anti-PD-1 or anti-PD-L1 therapy, or prior severe or persistent immune-related adverse events (irAE). Subjects are not permitted to have any concurrent chemotherapy, immunotherapy, biologic or hormonal therapy for cancer treatment, but concurrent use of hormones for non-cancer related conditions (e.g., insulin for diabetes and hormone replacement therapy) are allowed.

(b) Design of the Study

Figure 1:
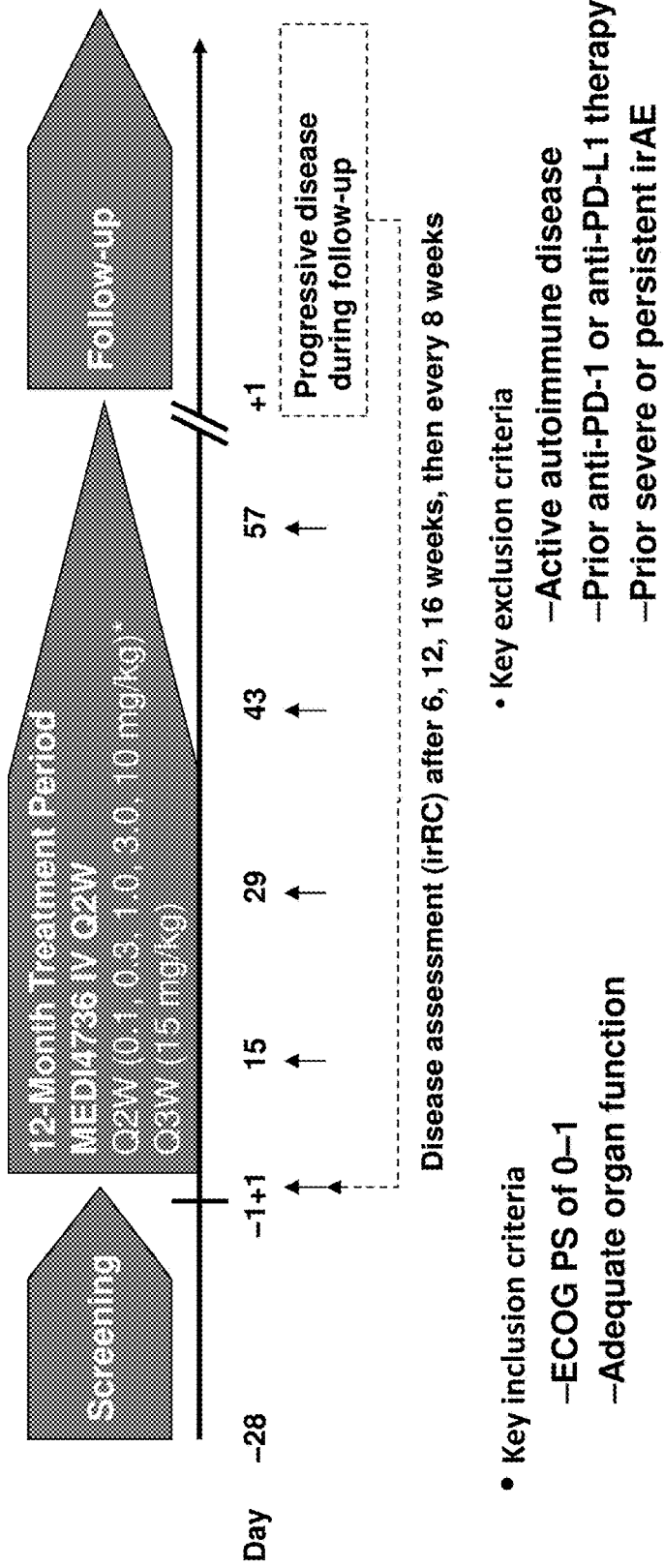
Figure 2A:
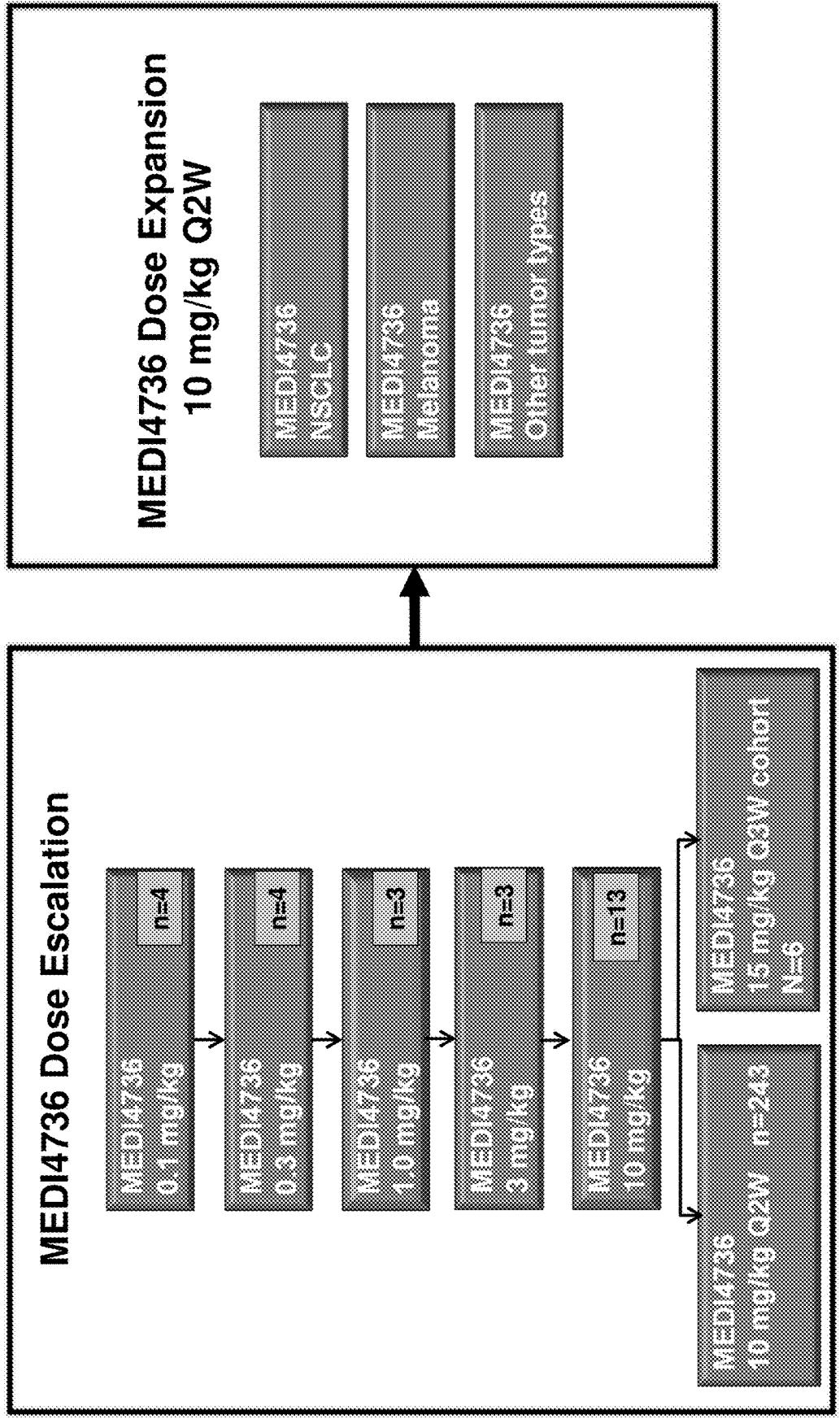
FIG. 2B shows the tumor types in the expansion.
Figure 2B:
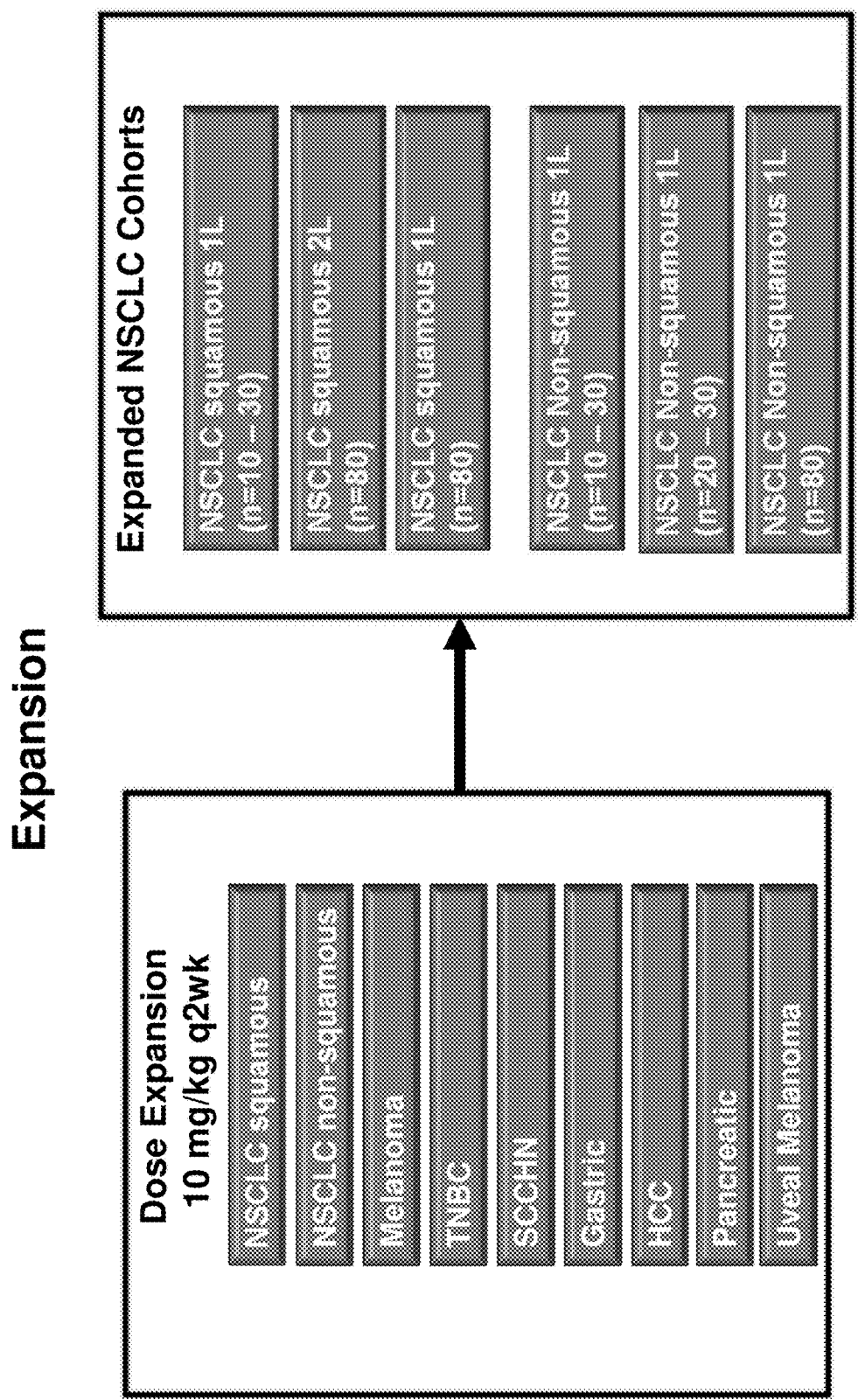

The study is a multicenter, open-label, Phase 1, first-time-in-human, dose-escalation and dose-expansion study in which multiple doses of MEDI4736 are administered via intravenous (IV) infusion to cancer patients. MEDI4736 was administered at 0.1, 0.3, 1, 3, 10, and 15 mg/kg doses. The study flow diagram is shown in FIG. 1. The first day of dosing is considered Day 1, and disease assessment takes place after 6, 12, and 16 weeks, and then every 8 weeks.

A dose-escalation was performed with administration every 2 weeks (Q2W) (+/−2 days) to different cohorts with doses of 0.1, 0.3, 1, 3, and 10 mg/kg doses.

A separate dose-escalation was performed with administration every 3 weeks (Q3W) at 15 mg/kg. An expansion phase is then conducted using the maximum tolerated dose (MTD) or optimal biological dose (OBD) identified in the dose-escalation.

A dose of 15 mg/kg Q2W may also be performed.

Dose Escalation

In the dose-escalation phase, the first dose of MEDI4736 was administered to all subjects in the first cohort as a 0.1 mg/kg infusion given over 4 hours. Subsequent infusions (2nd and 3rd doses, etc.) for the first cohort were given over 60 minutes Q2W. The doses for subsequent cohorts were 0.3, 1.0, 3.0, or 10 mg/kg, administered as a 60-minute IV infusion Q2W. A summary of the dose cohorts for the initial dose escalation is provided in Table 1 below. Additional doses of 15 mg/kg were also administered at Q3W.

TABLE 1

| Q2W Dosing Regimen | | |
|---|---|---|
| Dose Cohort | Number Subjects | Dosing Regimen |
| 1 | 3-6 | 0.1 mg/kg as a 4-hour IV infusion for the initial dose, and then as 60-minute IV infusion once every 2 weeks |
| 2 | 3-6 | 0.3 mg/kg as a 60-minute IV infusion once every 2 weeks |
| 3 | 3-6 | 1.0 mg/kg as a 60-minute IV infusion once every 2 weeks |
| 4 | 3-6 | 3.0 mg/kg as a 60-minute IV infusion once every 2 weeks |
| 5 | 3-6 | 10 mg/kg as a 60-minute IV infusion once every 2 weeks |
| 6 | 3-6 | 15 mg/kg as a 60-minute IV infusion once every 3 weeks |

With the completion of all cohorts in the Q2W dose escalation regimen, a separate dose escalation using the Q3W regimen begins and proceeds to a dose of up to 15 mg/kg Q3W based on available safety, PK/pharmacodynamics, and clinical data. The starting dose in the Q3W escalation is the equivalent dosing rate (in average mg/kg/week) to the optimal biological dose (OBD) (or highest dose tested if an OBD is not identified).

Subjects in the dose-escalation phase continue treatment until confirmed PD, initiation of alternative cancer therapy, unacceptable toxicity, or other reasons to discontinue treatment occur. In those subjects achieving confirmed disease control (DC), treatment may continue until 6 months past the date of confirmed DC. DC will include stable disease (SD) with a duration of 3 or more months, partial response (PR), and complete response (CR).

Dose Expansion

Following the completion of dose escalation at Q2W and Q3W, the dose regimen for the expansion phase is selected. Subjects enrolled in the dose expansion cohorts will receive MEDI4736 at the maximum tolerated dose (MTD), optimal biological dose (OBD), or the highest dose evaluated during dose escalation if no MTD or OBD is determined, given as an IV infusion at the selected dose and frequency. Subjects who achieve disease control (DC) will continue treatment and then enter the maintenance period. Upon evidence of progressive disease (PD) at any time during the maintenance period, MEDI4736 will be re-administered as an IV infusion until confirmed PD or other reason to discontinue MEDI4736.

Maintenance Period

Subjects who achieve disease control (DC) during the escalation or expansion phases enter the maintenance period in which treatment can continue until six months past the date of confirmed DC.

During the maintenance period, MEDI4736 is administered as an IV infusion every 2 months for 6 months. Physical examination of subjects will be performed at months 2, 4, and 6. After a 6-month period of every 2-month dosing, MEDI4736 is discontinued. Upon evidence of progressive disease (PD), MEDI4736 is re-administered as an IV infusion at a Q2W or Q3W schedule until confirmed PD, initiation of alternative cancer therapy, unacceptable toxicity, withdrawal of consent, or other reason to discontinue treatment, for a maximum of 2 years.

(c) Phamacokinetic, Anti-Tumor and Safety Assessments

Measurement of MEDI4736 concentrations in serum were performed using a validated immunoassay during the Q2W dose-escalation phase. Blood samples for pharmacokinetic assessment, as well as for soluble B7-H1 (sB7-H1) concentrations, were collected according to the following schedules during the Q2W dose-escalation phase:

First dose: Day 1 predose, end of infusion (EOI), and 3 hours after EOI, and Days 2, 3, 5, and 10 (+/−1 day). An additional sample at 2 hours after the start of the infusion was taken during the first study subject's initial, 4-hour infusion.

Second dose: Predose, EOI, 3 hours after EOI, and Day 8.

Subsequent even-numbered doses only: Predose and EOI.

Upon discontinuation or last dose, a pharmacokinetic (PK) sample should be drawn at 14 days, 30 days, 2 and 3 months after last dose.

For Q3W dosing, the pharmacokinetic assessments are performed at the same schedule as Q2W dosing except that a blood sample is also collected on Day 15 after the first dose. During the dose-expansion phase, pharmacokinetic assessments are performed every two months (Day 1 predose and EOI). In addition, upon discontinuation or last dose, a pharmacokinetic (PK) sample is drawn at 14 days, 30 days, 2 months, and 3 months after the last dose. During the maintenance phase, pharmacokinetic assessments and evaluations of sB7-H1 are performed on Days 14 and 30 (+/−3 days), and at months 2, 4, and 6 (+/−1 week).

The presence of anti-drug antibodies (ADA) was assessed (and will continue to be assessed) on Day 1 (preinfusion) and at all doses following dose 2 during the Q2W dose-escalation phase. ADA will be assessed according to the same schedule in the Q3W dose-escalation and dose-expansion phases. During the maintenance phase, ADA will be assessed at month 6 (+/−1 week).

Tumor assessments were performed (and will continue to be performed) during screening (day−28 to day−1) and at week 7 in the Q2W dose-escalation phase. Tumor assessments are performed with the same timing in the Q3W dose-escalation phase and the dose-expansion phase. Tumor assessments can include the following evaluations: physical examination (with photograph and measurement of skin lesions as applicable), CT, or MRI scan of the chest, abdomen, and pelvis, and CT or MRI scan of the brain. Computed tomography or MRI scan of the brain is performed only at screening or if the subject is neurologically symptomatic. During the maintenance phase, tumor assessments are performed at months 2, 4, and 6 (+/−1 week).

During the expansion phase, tumor biopsies are also performed during screening (day−28 to day−1) and at week 7.

Assessments of anti-tumor activity are based on the immune-related objective response rate (ORR), immune-related disease control rate (DCR), immune-related duration of response (DR), immune-related progression-free survival (PFS), and overall survival (OS). Immune-related response criteria (Wolchok et al., *Clin Cancer Res.* 15:7412-20 (2009)) were used to determine tumor response.

The ORR is defined as the proportion of subjects with confirmed complete response (CR) or confirmed partial response (PR). Confirmed responses are those that persist on repeat imaging study≥4 weeks after the initial documentation of response. The DCR is defined as the proportion of subjects with CR, PR or stable disease (SD) (subjects achieving SD will be included in the DCR if they maintain SD for ≥3 months). The 95% confidence interval (CI) of ORR and DCR is estimated using the exact probability method. The duration of response (DR) is the duration from the first documentation of objective response to the first documented disease progression. Progression-free survival (PFS) is measured from the start of treatment with MEDI4736 until the documentation of confirmed immune-related disease progression or death due to any cause, whichever occurs first. Overall survival (OS) is the time from the start of treatment with MEDI4736 until death.

Adverse events are monitored following administration of MEDI4736. Other assessments include physical examination, vital sign monitoring, and laboratory measurements.

Example 2: Results (a) Enrollment and Baseline Characteristics

The baseline characteristics of the subjects administered 0.1, 0.3, or 1 mg/kg MEDI4736 in the Q2W dose-escalation phase are provided in Table 2 below. In addition, 245 patients have been treated with 10 mg/kg Q2W and 6 patients have been treated with 15 mg/kg Q3W.

TABLE 2

Demographics for Q2W dosing

| Characteristic | 0.1 mg/kg (n = 4) | 0.3 mg/kg (n = 4) | 1.0 mg/kg (n = 3) | Total (N = 11) |
| --- | --- | --- | --- | --- |
| Mean Age (yrs) | 58.5 (46-65) | 68.0 (65-71) | 65.3 (43-77) | 63.8 (43-77) |
| Gender (male/female) | 2/2 | 3/1 | 1/2 | 6/5 |
| ECOG 1 at baseline (n) | 2 | 1 | 2 | 5 |
| ECOG 0 at baseline (n) | 2 | 3 | 1 | 6 |
| Mean number of prior cancer treatments (range) | 9.8 (5-17) | 5.8 (4-9) | 6.0 (1-10) | 7.3 (1-17) |

TABLE 2-continued

Demographics for Q2W dosing

| Characteristic | 0.1 mg/kg (n = 4) | 0.3 mg/kg (n = 4) | 1.0 mg/kg (n = 3) | Total (N = 11) |
|---|---|---|---|---|
| Colorectal tumor (n) | 0 | 1 | 0 | 1 |
| Melanoma (n) | 1 | 0 | 1 | 2 |
| NSCLC (n) | 3 | 3 | 2 | 8 |

The baseline characteristics of the subjects administered 0.1, 0.3, 1, 3, 10, or 15 mg/kg MEDI4736 in the Q2W and Q3W dose-escalation phases are provided in FIG. 3.

(b) Pharmacokinetics

Figure 5:
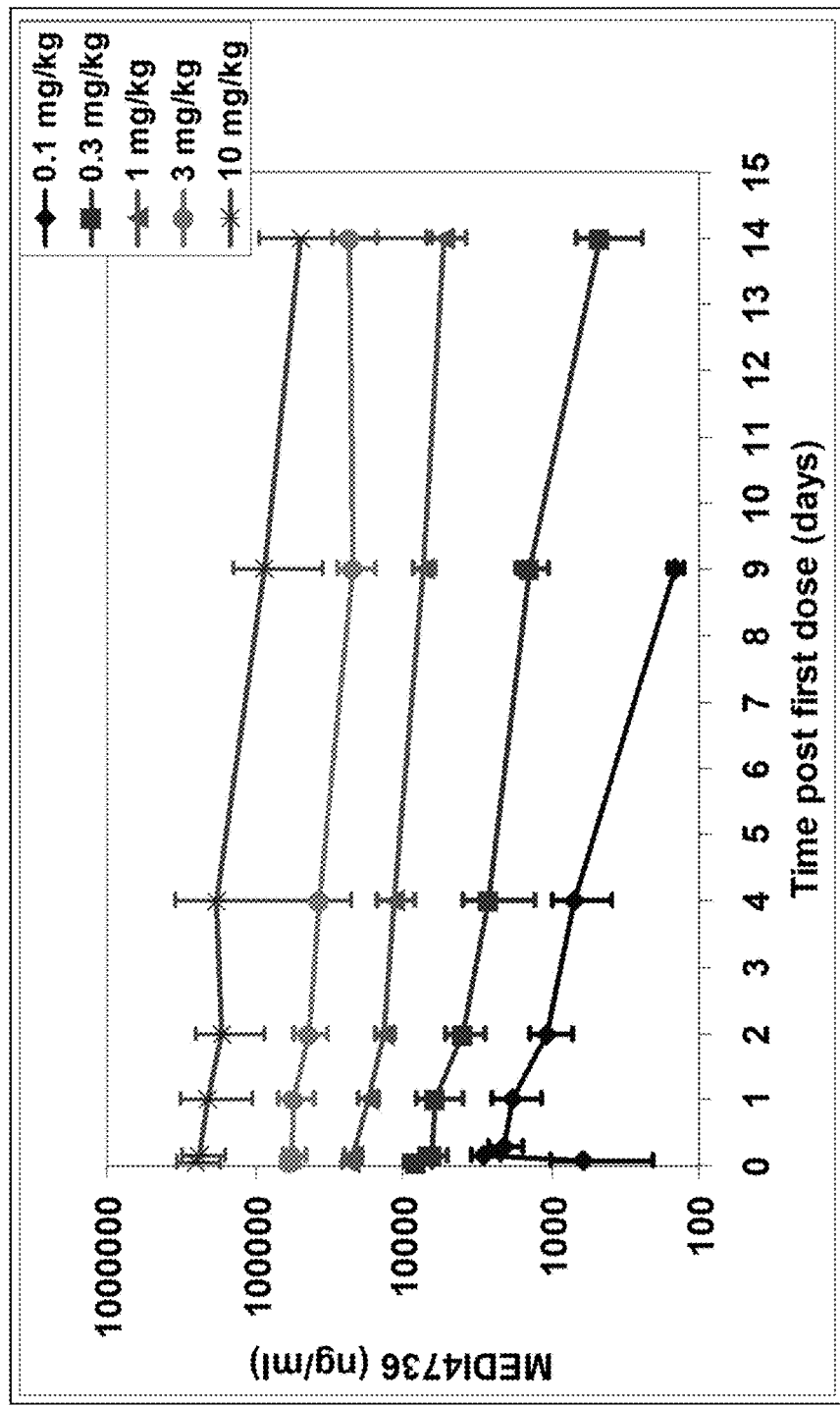
FIG. 5 shows the concentration of MEDI4736 over time that was observed in patients receiving 0.1 mg/kg, 0.3 mg/kg, 1 mg/kg, 3 mg/kg or 10 mg/kg MEDI4736 (Q2W) during the dose-escalation phase of the study.
Figure 6:
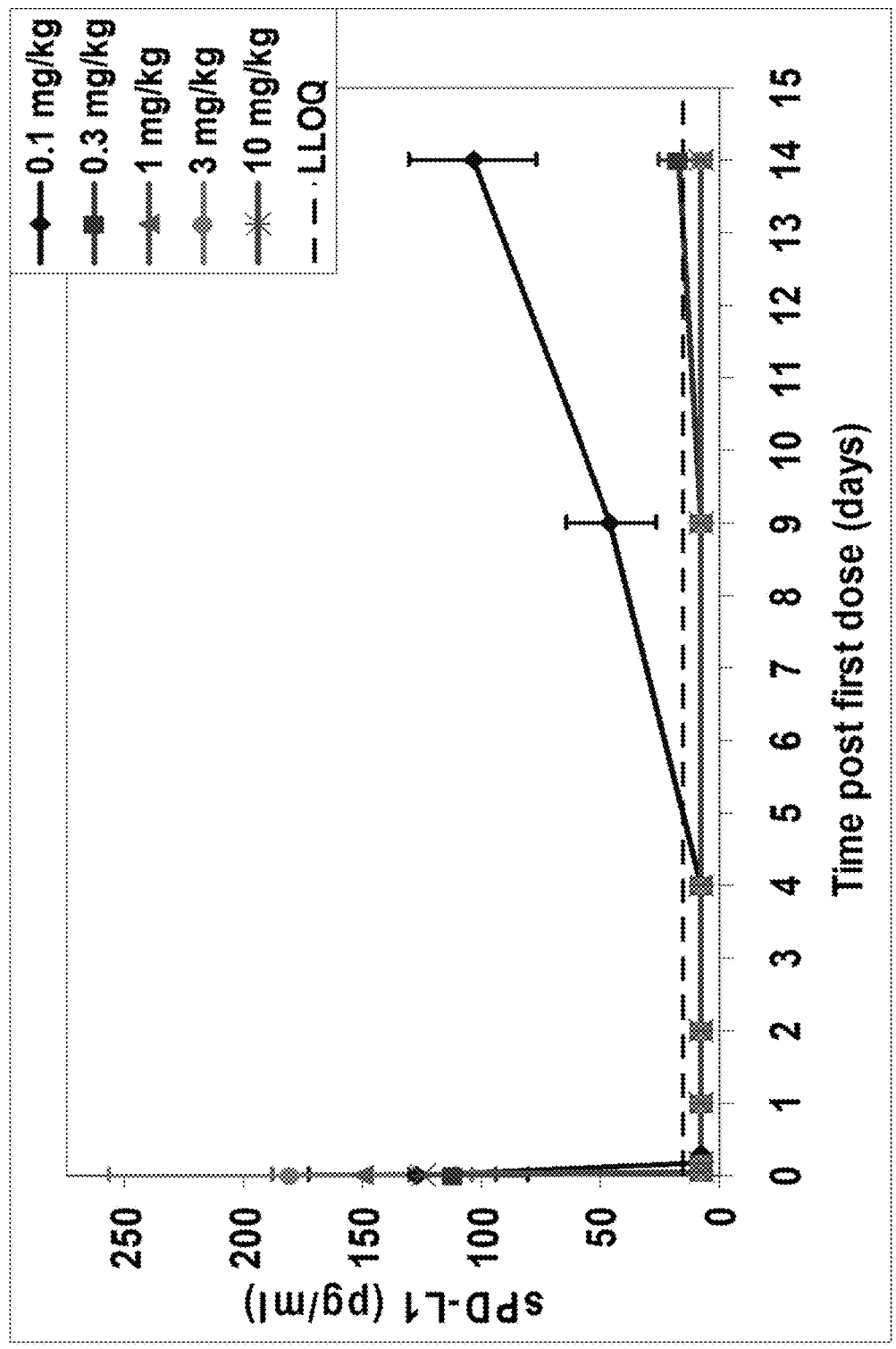
FIG. 6 shows the target engagement over time that was observed in patients receiving 0.1 mg/kg, 0.3 mg/kg, 1 mg/kg, 3 mg/kg or 10 mg/kg MEDI4736 (Q2W) during the dose-escalation phase of the study. "LLOQ"=lower limit of quantitation.

The pharmacokinetic data resulting from administration of MEDI4736 at 0.1 and 0.3 mg/kg in the Q2W dose-escalation phase is summarized in FIG. 4. MEDI4736 exhibited a non-linear PK at lower doses, but a linear PK with doses≥1.0 mg/kg Q2W. See FIG. 5. MEDI4736 also showed a dose-dependent increase in target engagement (FIG. 6), consistent with binding of MEDI4736 with B7-H1. Based on calculations using pK data and measurements of soluble B7-H1, significant target occupancy was achieved with doses≥0.3 mg/kg Q2W, and near complete saturation is expected at doses≥3 mg/kg Q2W. See FIG. 6.

(c) Efficacy

Tumor shrinkage was observed at all dose levels, including in heavily pretreated patients and in patients with large tumor burdens. Activity was apparent quickly (6 weeks) and was durable. Partial responses (PR) and stable disease (SD) were observed in patients receiving as little as 0.1 mg/kg Q2W. See FIG. 7 and Table 3 below.

| Dose (mg/kg) | Dosing Frequency | Subject ID | Number of Doses Received | Best Response | % Change in Tumor Burden |
|---|---|---|---|---|---|
| 0.1 | Q2W | 1056201004 | 25 | SD | −47.6 |
| 0.1 | Q2W | 1056201006 | 11 | PD | 50.3 |
| 0.1 | Q2W | 1245501002 | 3 | NE | NE |
| 0.1 | Q2W | 1245501003 | 8 | PD | 55.8 |
| 0.3 | Q2W | 1094301002 | 5 | PD | +>100 |
| 0.3 | Q2W | 1245501006 | 24 | PR | −60.1 |
| 0.3 | Q2W | 1351901002 | 1 | NE | NE |
| 0.3 | Q2W | 1351901004 | 22 | PR | −71.2 |
| 1 | Q2W | 1056201009 | 19 | SD | −46.6 |
| 1 | Q2W | 1094301003 | 18 | PR | −83.3 |
| 1 | Q2W | 1351901007 | 17 | PR | −76.8 |
| 3 | Q2W | 1056201010 | 5 | SD | −16.1 |
| 3 | Q2W | 1094301004 | 7 | PD | 38 |
| 3 | Q2W | 1351901008 | 3 | PD | +>100 |
| 10 | Q2W | 1002501208 | 5 | SD | 32.4 |
| 10 | Q2W | 1056201201 | 5 | PD | +>100 |
| 10 | Q2W | 1094301205 | 13 | SD | 9.3 |
| 10 | Q2W | 1245501206 | 5 | PD | 60 |
| 10 | Q2W | 1351901209 | 3 | PD | 82 |
| 10 | Q2W | 1371501207 | 2 | PD | 75.1 |
| 15 | Q3W | 1002501313 | 1 | NA | NA |
| 15 | Q3W | 1056201213 | 4 | SD | 16.4 |
| 15 | Q3W | 1245501211 | 5 | SD | −5 |
| 15 | Q3W | 1351901223 | 4 | SD | 10 |
| 15 | Q3W | 1371501297 | 2 | NA | NA |
| 15 | Q3W | 1372001228 | 5 | SD | 0 |

Figure 8:
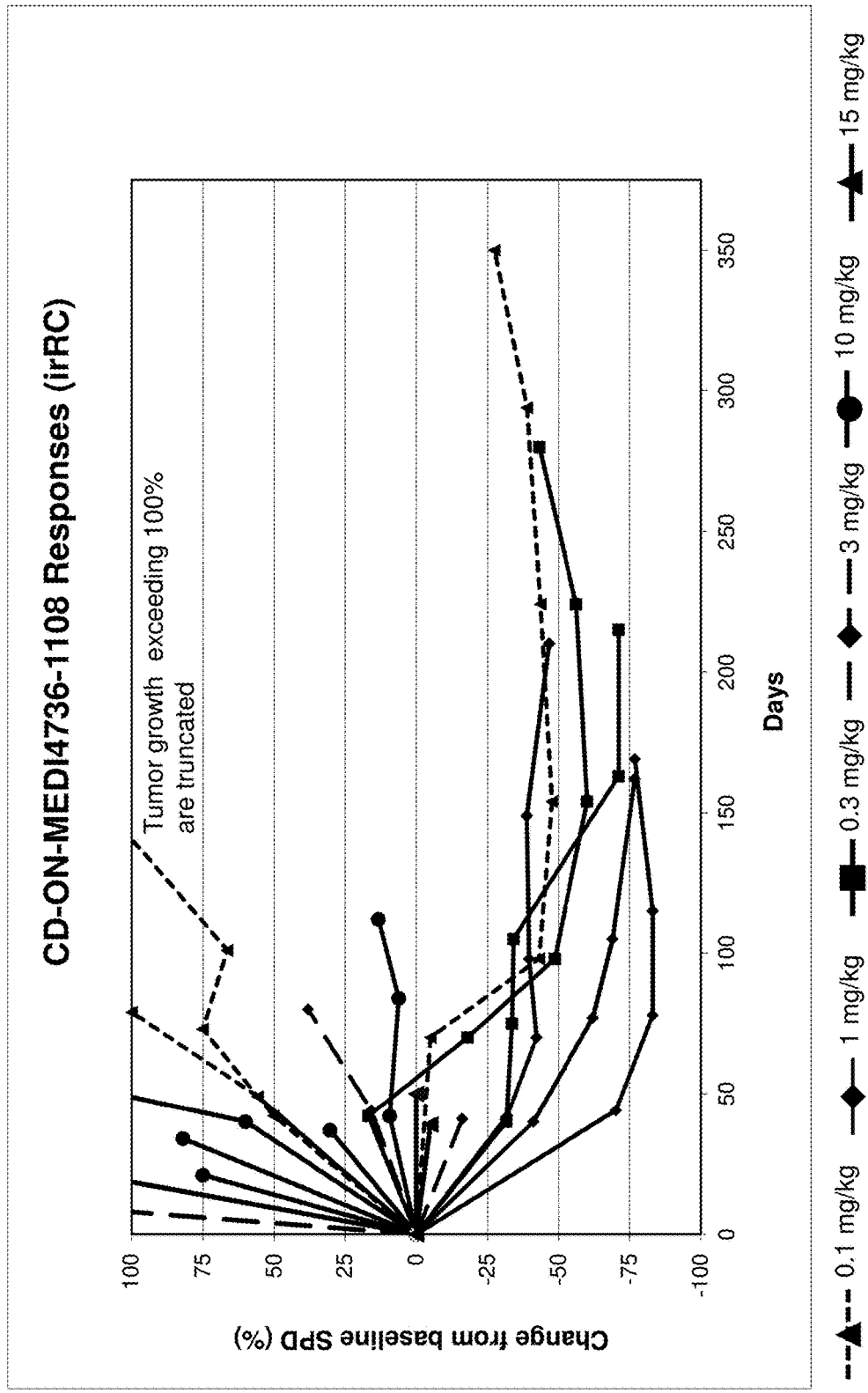
FIG. 8 shows the effect of MEDI4736 on tumor size in patients receiving 0.1 mg/kg, 0.3 mg/kg, 1 mg/kg, 10 mg/kg or 15 mg/kg MEDI4736.
Figure 9:
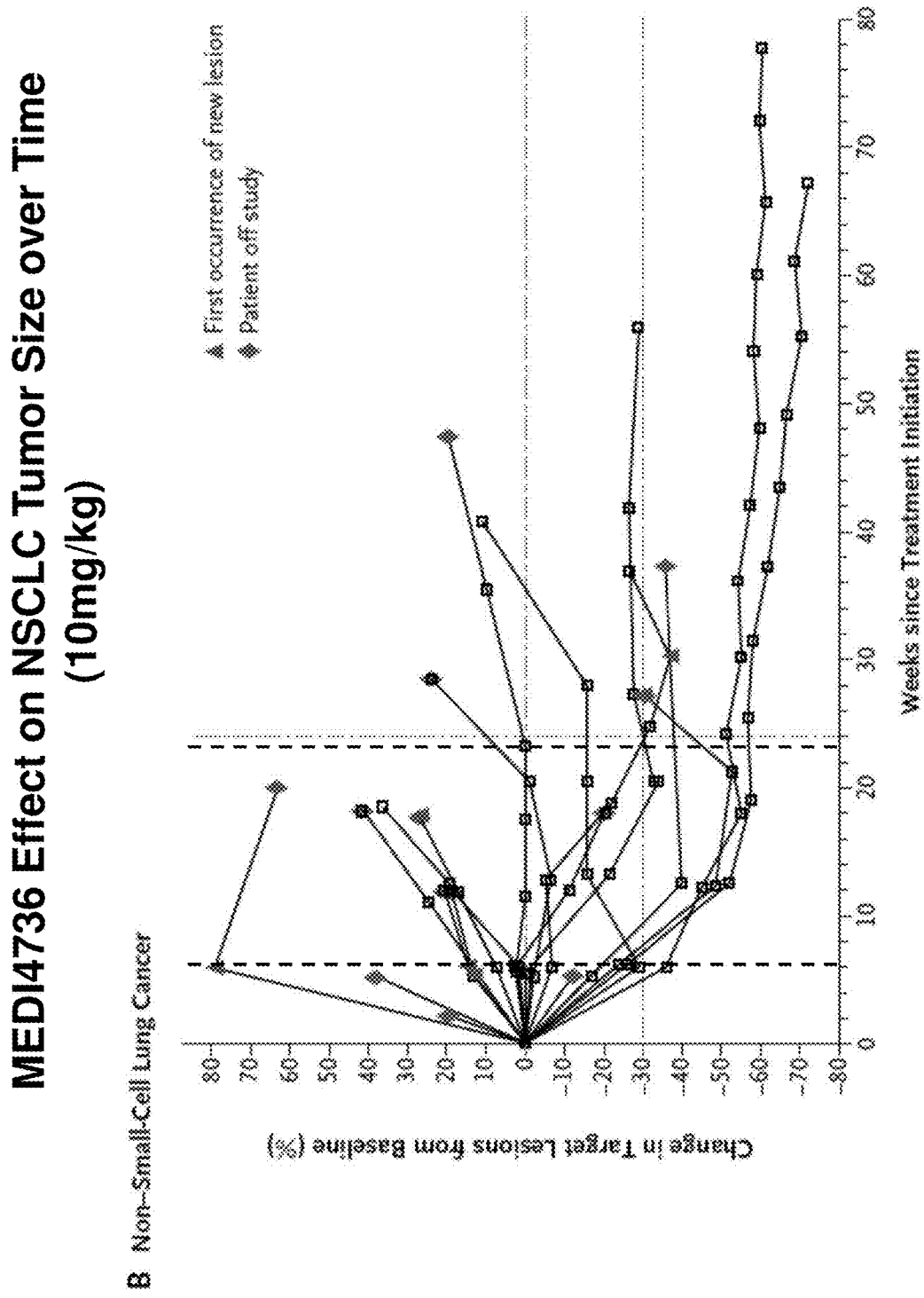
FIG. 9 shows effect of 10 mg/kg MEDI4736 on NSCLC tumors.

In addition, tumor burdens decreased as must as 83% in patients receiving up to 10 mg/kg Q2W. See FIGS. 7-9. For instance, one NSCLC adenocarcinoma patient (1351901004) receiving 0.3 mg/kg showed a 31% decrease in tumor burden after 6 weeks and a 71% decrease in tumor burden after 23 weeks. Prophylactic steroids were used in one subject and did not appear to affect clinical activity.

In the dose-expansion phase, clinical activity was initially observed in subjects with non-small cell lung cancer, melanoma, and pancreatic cancer. Stable disease (at 12 weeks) was observed in subjects with non-small cell lung cancer (non-squamous), pancreatic cancer, GI cancer, melanoma, and squamous cell carcinoma of the head and neck.

Figure 10:
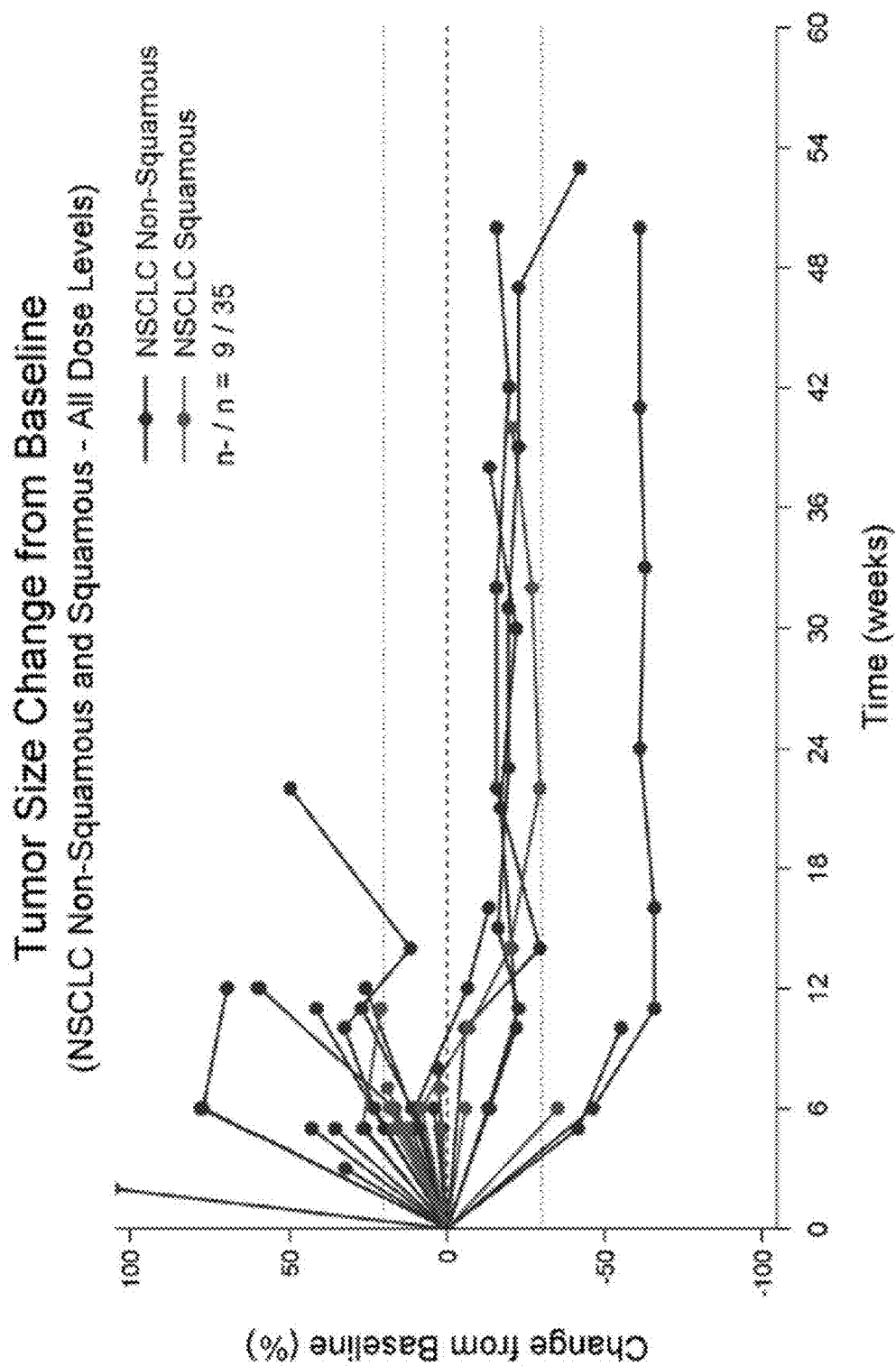
FIG. 10 shows the percent change of tumor size from baseline for all dose levels for NSCLC (Non-squamous and squamous).

The percent change of tumor size from baseline for all dose levels for NSCLC (Non-squamous and squamous) is shown in FIG. 10.

Figure 11:
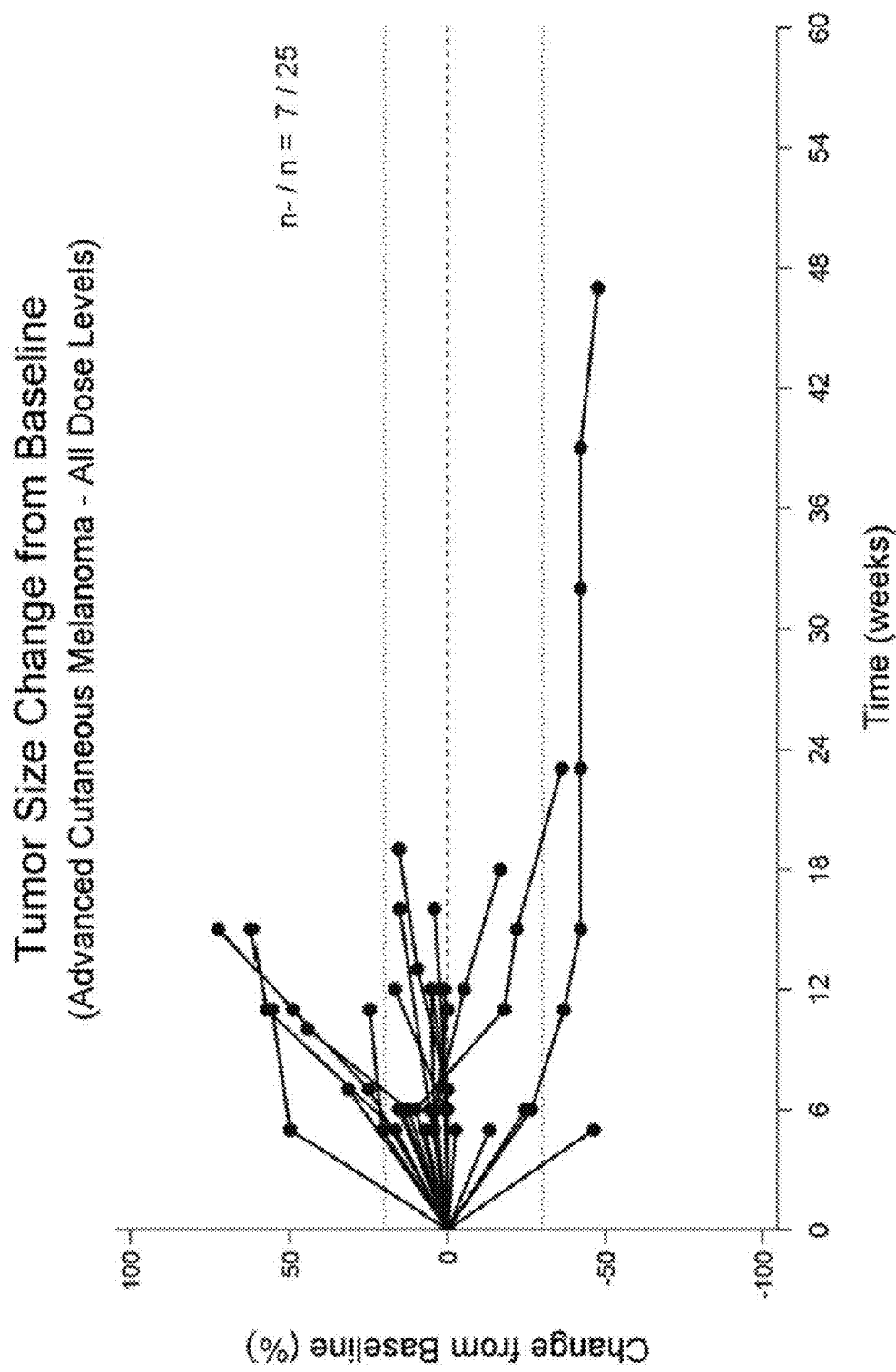
FIG. 11 shows the percent change of tumor size from baseline for all dose levels for advanced cutaneous melanoma.

The percent change of tumor size from baseline for all dose levels for advanced cutaneous melanoma is shown in FIG. 11.

Figure 12:
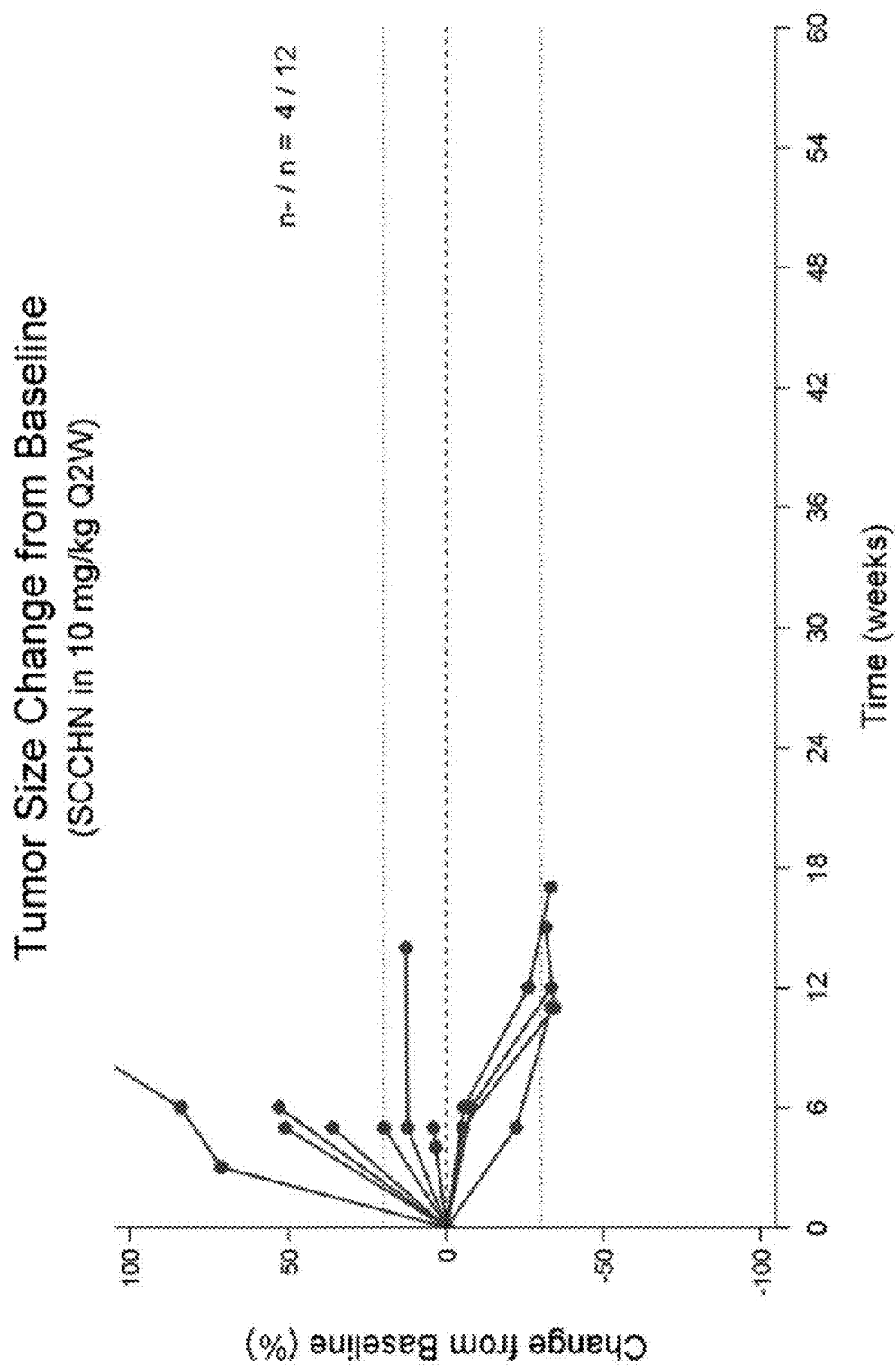
FIG. 12 shows the percent change of tumor size from baseline for SCCHN patients treated with 10 mg/kg MEDI4736 2QW.

The percent change of tumor size from baseline for SCCHN patients treated with 10 mg/kg MEDI4736 2QW is shown in FIG. 12.

The percent change of tumor size from baseline for pancreatic adenocarcinoma patients treated with 10 mg/kg MEDI4736 2QW is shown in FIG. 13. There are 8 subjects with SD [41-108 days] or better. Of these, 6 patients had ≥2 L of therapy prior to study enrollment. Seven of eight patients with SD or better are PD-L1(−)(the other patient's PD-L1 status is unknown).

The percent change of tumor size from baseline for gastroesophageal cancer patients treated with 10 mg/kg MEDI4736 2QW is shown in FIG. 14. There are 9 subjects with SD [35-174 days] or better. Of these, 6 had ≥2 L of therapy prior to study enrollment. Three patients with SD or better are PD-L1(−), 2 are PD-L1(+) and the rest are unknown.

The percent change of tumor size from baseline for hepatocellular carcinoma (HCC) patients treated with 10 mg/kg MEDI4736 2QW is shown in FIG. 15. Of the 17 patients enrolled, all have received Sorafenib previously. Three are HBV(+), 2 are HCV(+) and the rest are HBV(−) & HCV(−). There are 5 subjects with SD [33-76 days] or better. Of these, 4 of them have had ≥2 L of therapy prior to enrollment; 1 HBV(+); 4 HBV(−) & HCV(−). Three patients with SD or better are PD-L1(−) and the PD-L1 status is unknown in the rest of these patients.

The percent change of tumor size from baseline for triple negative breast cancer (TNBC) patients treated with 10 mg/kg MEDI4736 2QW is shown in FIG. 16.

The percent change of tumor size from baseline for uveal melanoma patients treated with 10 mg/kg MEDI4736 2QW is shown in FIG. 17.

A comparison of the percent change in tumor size from baseline for NSCLC patients treated with 10 mg/kg MEDI4736 2QW evaluable for 2 scans is shown in FIG. 18A. The plot shows patients with PD-L1 Positive tumors, PD-L1 Negative tumors and patients whose PD-L1 tumor status was not available. Patients that were identified as smokers are shown with a star. The ORR (confirmed CR+PR) for all patients was 3.7%. The ORR rate for PD-L1+patients was 10%.

A comparison of the percent change in tumor size from baseline for NSCLC patients treated with all dose levels of MEDI4736 2QW evaluable for 1 scan is shown in FIG. 18B. The plot shows patients with PD-L1 Positive tumors, PD-L1 Negative tumors and patients whose PD-L1 tumor status was not available. Patients that were identified as smokers are shown with a star. The ORR (confirmed CR+PR) for all confirmed patients was 4.3% (ORR for all unconfirmed patients was 8.5%). The ORR rate for PD-L1+patients was 8.3%.

The change in tumor size for 6 tumor types in the Escalation Phase are shown in FIG. 19.

The response of one patient in the Expansion Phase treated with 10 mg/kg MEDI4736 Q2W is shown in FIG. 20. In the upper left Panel, the patient tumor is marked. After week 6, the tumor has shrunk as shown in the upper right panel.

A dramatic effect of tumor regression in a patient with SCCHN (PD-L1+) after only two infusions of MEDI4736 (10 mg/kg Q2W) is shown in FIG. 21.

PD-L1 Staining

PD-L1 staining in tumor tissue from a panel of tumors was performed to assess level of PD-L1 in various tumors by IHC. The results are shown in Table 4.

TABLE 4

| Tumor | N Examined | N PD-L1 Positive | % Positive |
|---|---|---|---|
| NSCLC - SCC | 75 | 22 | 29.3 |
| NSCLC - Adeno | 36 | 12 | 33.3 |

TABLE 4-continued

| Tumor | N Examined | N PD-L1 Positive | % Positive |
|---|---|---|---|
| Small Cell LC | 37 | 2 | 5.4 |
| Breast - TN | 42 | 11 | 26.2 |
| Head and Neck SCC | 18 | 3 | 16.7 |
| Gastric | 20 | 3 | 15.0 |
| HCC | 40 | 4 | 10.0 |
| Urinary Bladder | 18 | 2 | 11.1 |
| Uveal Melanoma | 12 | 3 | 25.0 |
| Mesothelioma | 20 | 1 | 12.6 |
| Pancreas | 25 | 1 | 3.6 |
| CRC | 32 | 1 | 3.1 |
| RCC | 20 | 0 | 0.0 |
| Ovarian | 48 | 0 | 0.0 |

The 10 mg/kg Q2W dose (N=245) was well tolerated. The most frequent SAEs are shown in Table 5 below:

TABLE 5

| | Q2W | | | | | Q3W |
|---|---|---|---|---|---|---|
| | 0.1 mg/kg N = 4 | 0.3 mg/kg N = 4 | 1 mg/kg N = 3 | 3 mg/kg N = 3 | 10 mg/kg N = 245 | 15 mg/kg N = 6 |
| | Top 15 most frequent AE by preferred term | | | | | |
| Fatigue | 1 (25.0%) | 2 (50.0%) | 1 (33.3%) | 0 (0.0%) | 68 (27.8%) | 3 (50.0%) |
| Dyspnoea | 1 (25.0%) | 2 (50.0%) | 1 (33.3%) | 1 (33.3%) | 40 (16.3%) | 1 (16.7%) |
| Nausea | 0 (0.0%) | 1 (25.0%) | 2 (66.7%) | 0 (0.0%) | 37 (15.1%) | 2 (33.3%) |
| Decreased Appetite | 0 (0.0%) | 1 (25.0%) | 1 (33.3%) | 0 (0.0%) | 32 (13.1%) | 0 (0.0%) |
| Constipation | 0 (0.0%) | 1 (25.0%) | 1 (33.3%) | 1 (33.3%) | 28 (11.4%) | 0 (0.0%) |
| Pyrexia | 0 (0.0%) | 3 (75.0%) | 0 (0.0%) | 1 (33.3%) | 21 (8.6%) | 2 (33.3%) |
| Cough | 1 (25.0%) | 1 (25.0%) | 0 (0.0%) | 1 (33.3%) | 20 (8.2%) | 3 (50.0%) |
| Abdominal Pain | 0 (0.0%) | 1 (25.0%) | 1 (33.3%) | 0 (0.0%) | 20 (8.2%) | 1 (16.7%) |
| Diarrhoea | 1 (25.0%) | 2 (50.0%) | 1 (33.3%) | 0 (0.0%) | 19 (7.8%) | 0 (0.0%) |
| Rash | 1 (25.0%) | 2 (50.0%) | 2 (66.7%) | 0 (0.0%) | 18 (7.4%) | 0 (0.0%) |
| Vomiting | 1 (25.0%) | 1 (25.0%) | 0 (0.0%) | 0 (0.0%) | 20 (8.2%) | 1 (16.7%) |
| Dizziness | 0 (0.0%) | 1 (25.0%) | 2 (66.7%) | 0 (0.0%) | 17 (6.9%) | 0 (0.0%) |
| Headache | 1 (25.0%) | 1 (25.0%) | 1 (33.3%) | 0 (0.0%) | 16 (6.5%) | 1 (16.7%) |
| Pruritus | 0 (0.0%) | 0 (0.0%) | 1 (33.3%) | 0 (0.0%) | 19 (7.8%) | 0 (0.0%) |
| Chills | 0 (0.0%) | 1 (25.0%) | 0 (0.0%) | 0 (0.0%) | 17 (6.9%) | 0 (0.0%) |

(d) Safety and Anti-Drug Antibodies

MEDI4736 was generally well tolerated. No pneumonitis, colitis (of any grade), or hyperglycemia was observed. In addition, no treatment-related Grade≥3 events were observed in the 0.1 to 3 mg/kg cohorts. No dose-limiting toxicities were observed. A summary of the Adverse Events for the 6 cohorts is shown in Table 6 below:

TABLE 6

Summary of Safety - Adverse Event Overview

| | Q2W | | | | | Q3W |
|---|---|---|---|---|---|---|
| | 0.1 mg/kg N = 4 | 0.3 mg/kg N = 4 | 1 mg/kg N = 3 | 3 mg/kg N = 3 | 10 mg/kg N = 245 | 15 mg/kg N = 6 |
| Any AE | 4 (100%) | 4 (100%) | 3 (100%) | 3 (100%) | 178 (72.7%) | 6 (100%) |
| G3/4 AE | 1 (25.0%) | 0 | 1 (33.3%) | 1 (33.3%) | 60 (24.5%) | 2 (33.3%) |
| SAE | 1 (25.0%) | 2 (50.0%) | 1 (33.3%) | 1 (33.3%) | 49 (20.0%) | 2 (33.3%) |
| AE to D/C | 1 | 1 (25.0%) | 0 | 0 | 15 (6.1%) | 0 |
| Related AE | 2 (50.0%) | 1 (25.0%) | 1 (33.3%) | 1 (33.3%) | 82 (33.5%) | 5 (83.3%) |
| Related G3/4 AE | 0 | 0 | 0 | 0 | 12 (4.9%) | 1 (16.7%) |
| Related AE to D/C* | 0 | 0 | 0 | 0 | 1 (0.4%) | 0 |

An extremely low incidence of ADAs was observed over the dose range of 0.1 to 3 mg/kg. In particular, only 1 of 15 patients who received a dose of dose range of 0.1 to 1 mg/kg tested ADA positive with PK/PD implications. There was no evidence for impact on drug exposure or target suppression over the dose range of 0.1 to 1.0 mg/kg.

(e) Discussion

This study demonstrates that MEDI4736 has favorable pK properties and is generally well tolerated. In addition, MEDI4736 is effective in treating solid tumors (including, but not limited to melanoma, non-small cell lung cancer, pancreatic adenocarcinoma, uveal melanoma, squamous cell carcinoma of the head and neck, gastroesophageal cancer, and hepatocellular carcinoma) while producing a low incidence of ADA. Clinical benefit was observed at all dose levels tested, with activity reported as early as 6 weeks.

Example 3: Quantitation of Soluble B7-H1

Soluble B7-H1 (not bound to MED4736) was measured using an electrochemiluminescent (ECL) based assay. The specific procedure used to assay soluble B7-H1 in human serum is shown below.

(a) Plate Preparation

I-Block Buffer (IBB) (MedImmune) was equilibrated to room temperature (RT) and transferred to a reagent reservoir (Fisher Scientific #07-200-127). 150 μl of IBB was pipetted into each plate well of streptavidin-coated plates (Meso Scale Discovery ("MSD") Cat. L11SA/L15SA). The plates were covered and incubated at RT for a minimum of one hour (no more than four hours) with shaking at approximately 450 rpm on an orbital plate shaker.

Capture Antibody Working Solution (WS) was prepared immediately before use using IBB at RT. The capture antibody is a biotinylated anti-human B7-H1 IgG1 TM antibody, clone 2.7A4 as described in US 2013/0034559. First, at least 100 μL of capture antibody stock solution was pre-diluted in IBB to a concentration of 1000 μg/ml as shown in Table 7 below. Then, 250 μg/mL Capture Antibody WS was prepared in IBB in polypropylene tubes using the volumes indicated in Table 8 below. Capture Antibody WS was then transferred to a reagent reservoir.

TABLE 7

Pre-dilution of Capture Antibody Stock Solution assuming stock concentration of 10 mg/mL

| Solution | Target Concentration | IBB Vol (μL) | Source Solution | Source Solution Vol (μL) | Dilution Factor |
| --- | --- | --- | --- | --- | --- |
| Capture Antibody Pre-Dilution (PD) | 1000 μg/mL | 90 | Capture Antibody Stock Solution | 10 | 10 |

TABLE 8

Preparation of Capture Antibody WS from Capture Antibody PD

| Solution | Target Concentration | IBB Vol (μL) | Source Solution | Source Solution Vol (μL) | Dilution Factor |
| --- | --- | --- | --- | --- | --- |
| Pre-Dilution A | 10 μg/mL | 990 | Capture Antibody PD | 10 | 100 |
| Capture Antibody WS | 250 ng/mL | 7800 | Pre-Dilution A | 200 | 40 |

Plate blocking was ended by washing plates with 3×300 μL 1×ELISA Wash Buffer (1×PBS, 0.05% Tween 20) using plate washer. Plates were blotted dry and immediately coated with 35 μL per well of Capture Antibody WS. Plates were sealed and incubated for 1 hour at RT while shaking at approximately 450 rpm on an orbital plate shaker.

(b) Test Sample, Reference Sample, and Quality Control Sample Preparation

Human serum samples to be tested were thawed at RT and gently mixed until uniform. These samples were used undiluted.

Reference Standard Stock Solutions (RS Stock) of recombinant B7-H1 were pre-diluted in Assay Matrix (AM): Neal Calf Serum (Lonza, Cat 14-401F) to a concentration of 47 μg/mL as indicated in Table 9 below. RS Pre-Dilution was serially diluted in AM as indicated in Table 10 below for final reference standard concentrations of 2000 (S1), 1000 (S2), 500 (S3), 250 (S4), 125 (S5), 62.5 (S6), 31.3 (S7), 15.6 (S8), 7.8 (S9), and 3.9 (S10) pg/mL. An AM-alone sample was also included. Dilutions were prepared in polypropylene titer tubes or equivalent.

TABLE 9

Pre-dilution of Reference Standard Stock Solution assuming RS Stock Concentration of 470 μg/mL.

| Solution | Target Concentration | Assay Matrix Vol (μL) | Source Solution | Source Solution Vol (μL) | Dilution Factor |
| --- | --- | --- | --- | --- | --- |
| RS Pre-Dilution | 47 μg/mL | 90 | RS Stock, 470 μg/mL | 10 | 10 |

TABLE 10

Preparation of Reference Standard Dilutions

| Solution | Target Concentration | Assay Matrix Vol (μL) | Source Solution | Source Solution Vol (μL) | Dilution Factor |
| --- | --- | --- | --- | --- | --- |
| Pre-Dilution A | 4700 μg/mL | 90 | RS Pre-Dil. 47 μg/mL | 10 | 10.0 |
| Pre-Dilution B | 47 ng/mL | 990 | Pre-Dilution A | 10 | 100.0 |
| S1 | 2000 pg/ml | 800 | Pre-Dilution B | 35.6 | 23.5 |

TABLE 10-continued

Preparation of Reference Standard Dilutions

| Solution | Target Concentration | Assay Matrix Vol (µL) | Source Solution | Source Solution Vol (µL) | Dilution Factor |
|---|---|---|---|---|---|
| S2 | 1000 pg/ml | 400 | S1 | 400 | 2.0 |
| S3 | 500 pg/ml | 400 | S2 | 400 | 2.0 |
| S4 | 250 pg/ml | 400 | S3 | 400 | 2.0 |
| S5 | 125 pg/ml | 400 | S4 | 400 | 2.0 |
| S6 | 62.5 pg/ml | 400 | S5 | 400 | 2.0 |
| S7 | 31.3 pg/mL | 400 | S6 | 400 | 2.0 |
| S8 | 15.6 pg/mL | 400 | S7 | 400 | 2.0 |
| S9 | 7.8 pg/mL | 400 | S8 | 400 | 2.0 |
| S10 | 3.9 pg/mL | 400 | S9 | 400 | 2.0 |
| AM | 0 pg/mL | 400 | N/A | N/A | N/A |

Quality Control (QC) sample Pre-Dilutions in AM as well as High, Medium, and Low QC samples were prepared in polypropylene tubes or equivalent as indicated in Table 11 below. The QC stock solution used was recombinant B7-H1 protein in 90% calf serum (Lonza, Cat. 14-401F).

TABLE 11

Preparation of QC Sample Dilutions

| Solution | Target Concentration | Assay Matrix Vol (µL) | Source Solution | Source Solution Vol (µL) | Dilution Factor |
|---|---|---|---|---|---|
| Pre-Dilution A | 4700 µg/mL | 90 | QCS, 47 µg/mL | 10 | 10.0 |
| Pre-Dilution B | 47 ng/mL | 990 | Pre-Dilution A | 10 | 100.0 |
| Pre-Dilution C | 4.7 pg/ml | 180 | Pre-Dilution B | 20 | 10.0 |
| Pre-Dilution D | 0.47 pg/ml | 180 | Pre-Dilution C | 20 | 10.0 |
| QC1 (High) | 800 pg/ml | 400 | Pre-Dilution B | 6.9 | 58.8 |
| QC2 (Med) | 200 pg/ml | 400 | Pre-Dilution C | 17.8 | 23.5 |
| QC3 (Low) | 32 pg/ml | 400 | Pre-Dilution D | 29.2 | 14.7 |

(c) Soluble B7-H1 Detection

Prepared plates were washed with 3×300 µL 1×ELISA Wash Buffer and blotted dry. Test Samples, Reference Standards, Quality Controls, and Assay Matrix alone were transferred into duplicate wells on plates (35 µl each). Plates were sealed and incubated for 30 minutes at RT with shaking at approximately 450 rpm on an orbital plate shaker.

Primary Detection Antibody Working Solution (WS) was prepared in IBB (1 µg/mL) in polypropylene tubes as indicated in Table 12 below. The primary detection antibody was mouse anti-human B7-H1 IgG1 antibody clone 130021 (R&D Systems, Cat. MAB1561) (0.5 mg/ml).

TABLE 12

Preparation of Primary Detection Antibody Working Solution (WS)

| Solution | Target Concentration | IBB Vol (µL) | Source Solution | Source Solution Vol (µL) | Dilution Factor |
|---|---|---|---|---|---|
| Primary Detection Antibody WS | 1 µg/mL | 8000 | Primary Detection Antibody Stock Solution, 500 µg/mL | 16 | 500 |

Plates were removed from the shaker and washed 3×300 µL 1×ELISA Wash Buffer and blotted dry. Primary Detection Antibody WS was transferred into a reagent reservoir, and then 35 µl was pipetted into each plate well. The plates were sealed again and incubated at RT for an hour with shaking at approximately 450 rpm on an orbital plate shaker.

Secondary Detection Antibody Working Solution (WS) was prepared in IBB (1 µg/mL) in polypropylene tubes as indicated in Table 13 below. The secondary detection antibody was ruthenium-labeled goat anti-mouse B7-H1 polyclonal antibody (MSD, Cat. R32AC-1) (0.5 mg/ml). Secondary Detection Antibody WS was protected from light.

TABLE 13

Preparation of Secondary Detection Antibody Working Solution (WS)

| Solution | Target Concentration | IBB Vol (µL) | Source Solution | Source Solution Vol (µL) | Dilution Factor |
|---|---|---|---|---|---|
| Secondary Detection Antibody WS | 1 µg/mL | 8000 | Secondary Detection Antibody Stock Solution, 500 µg/mL | 16 | 500 |

Plates were removed from shaker and washed 3×300 µL 1×ELISA Wash Buffer and blotted dry. Secondary Detection Antibody WS was transferred into a reagent reservoir, and then 35 µl was pipetted into each plate well. The plates were sealed again and incubated at RT for an hour with shaking at approximately 450 rpm on an orbital plate shaker while protected from light.

Read Buffer T (1×) was prepared by diluting Read Buffer T (4×) (MSD Cat. R92TC-1) reagent in Cell Culture-Grade Water in polypropylene tubes as indicated in Table 14 below.

TABLE 14

Preparation of Secondary Detection Antibody Working Solution (WS)

| Solution | Target Concentration | Cell Culture-Grate Water Vol (μL) | Source Solution | Source Solution Vol (μL) | Dilution Factor |
|---|---|---|---|---|---|
| 1x Read Buffer T | 1x | 15 | 4x Read Buffer T | 5 | 4 |

Plates were removed from shaker and washed 3×300 μL 1×ELISA Wash Buffer. Plates were covered and blotted dry only immediately before addition of 1×READ Buffer T. Read Buffer T (1×) was transferred into a reagent reservoir. Assay plates were uncovered to be read and blotted dry. Read Buffer T (1×) was pipetted into all wells of the assay plate (150 μl), and the plate was read within 5 minutes.

(d) Data Analysis

Data was transferred into SoftMax® Pro GxP v. 5.2 software (Molecular Devices) for analysis, and the Reference Standard concentrations were plotted against the ECL signal values using a $1/y^2$ weighted 4-parameter logistical curve fitting model.

The pg/ml of sB7-H1 for all Reference Standards and QC sample dilutions were (back-)calculated. The coefficient of variation (% CV) of duplicate wells for each Reference Standard and QC sample dilution was also calculated. These data were used to determine if a plate met the Acceptance Criteria. A plate was considered valid if the following Acceptance Criteria were met:

1—the mean % recovery for Reference Standards levels S2 to S7 was within ±25% and level S8 was within ±30% of the nominal concentration;
2—the % CV for each back-calculated concentration of Reference Standard levels S2 to S7 was ≤25%, and level S8≤30%;
3—the mean % recovery for each QC level was within ±25% of the nominal concentration; and
4—the % CV for the back-calculated concentration for at least 2 out of 3 QC levels was ≤25%.

For valid plates, the pg/ml of sB7-H1 in each sample was calculated using the Reference Standard. Since Test Samples were tested neat, the dilution factor for each Test Sample is 1.0, and no dilution factor correction was needed. The resulting data represents sB7-H1 concentrations in 100% serum.

The data for the Test Samples was also reviewed to determine if it met the Acceptance Criteria. Test Sample readings were considered valid if the following Acceptance Criteria were met:

1—the back-calculated concentration of both replicates fell within the assay working range;
2—the % CV for the mean back-calculated concentration of the Test Sample was ≤25%.

In the event that the back-calculated concentration for one of the Test samples fell within the assay working range and the other below the assay lower limit of quantitation (LLOQ) or above the assay upper limit of quantitation ULOQ the following criteria were applied:

If the % CV of the mean back-calculated concentration is >25%, the test sample was considered invalid.
If the % CV of the mean back-calculated concentration was ≤25% and the mean back-calculated concentration was within the assay working range, the Test Sample was considered valid and the mean back-calculated concentration of the Test Sample was reported.
If the % CV of the mean back-calculated concentration was ≤25%, the Test Sample was considered valid and was reported as below the limit of quantitation or above the limit of quantitation.

In the event that the back-calculated concentration for both Test Sample replicates fell below the assay LLOQ, the Test Sample was considered valid and reported as below the limit of quantitation.

In the event that the back-calculated concentration for one of the Test Sample replicates fell below the assay working range and the other replicate was out of range, the following criteria were applied:

If the ECL value of the out of range replicate was below the mean LLOQ ECL of the assay, the Test Sample was considered valid and reported as below the limit of quantitation.
If the ECL value of the out of range replicate was above the mean ULOQ ECL of the assay, the Test Sample was considered invalid.

In the event that the back-calculated concentration for both Test Sample replicates fell above the assay ULOQ, the Test Sample was considered valid and reported as above the limit of quantitation.

In the event that the back-calculated concentration for one of the Test Sample replicates fell above the assay working range and the other replicate was out of range the following criteria were applied:

If the ECL value of the out of range replicate was above the mean ULOQ ECL of the assay, the Test Sample was considered valid and reported as above the limit of quantitation.
If the ECL value of the out of range replicate was below the mean LLOQ ECL of the assay, the Test Sample was considered invalid.

In the event that the back-calculated concentration for one of the Test Sample replicates fell within the assay working range and the other replicate was out of range, the Test Sample was considered invalid.

In the event that the back-calculated concentration for both Test Sample replicates was out of range the following criteria were applied.

If both ECL values fell below the mean LLOQ ECL of the assay, Test Sample was considered valid and reported as below the limit of quantitation.
If both ECL values fell above the mean ULOQ ECL of the assay, the Test Sample was considered valid and reported as above the limit of quantitation.
If the ECL value of one replicate was below the mean LLOQ ECL of the assay and the ECL value of the other replicate was above the ULOQ ECL, the Test Sample was considered invalid.

These procedures were used to determine the soluble B7-H1 in human serum samples as provided above in Examples 1 and 2 above.

Example 4: PD-L1 Expression Drives Patient Response Rate

Subject tissue of NSCLC patients was characterized for PDL1 expression by immunohistochemistry in formalin fixed and paraffin embedded tissue samples. A sample was determined to be "PD-L1 positive" if the sample contained 25% or more tumor cells with PDL1 membrane staining. The prevalence of such samples in the NSCLC population using the PDL1 assay was 20-40%.

A cutoff and scoring algorithm has been determined by evaluating samples from ~60 patients in the Phase I trial (CP1108). With the cutoff established for Phase 3 trials, approximately 40% of NSCLC patients are PD-L1 positive (Table 15, below).

TABLE 15

PD-L1 Expression is a Key Driver of Response

| Agent | PDL1+ | PDL1− | PDL1+ Population-NSCLC |
|---|---|---|---|
| MEDI4736 | 39%* (5/13) | 5%* (1/19) | 39% (24/62) |

*Patients treated <12 wks prior to the data cut censored

Patients identified as having PDL1-expressing tumors are more likely to respond to MEDI4736 treatment than unselected patients (Table 16, below). There was an objective response rate of fifty percent in PDL1-positive NSCLC patients treated with 10 mg/kg MEDI4736 for greater than 16-24 weeks (Table 16). This dramatic response rate was not observed in PDL1 negative or unselected patients (Table 16). These results indicate that PDL1 expression is a key driver of response in NSCLC.

TABLE 16

Objective Response Evolves Over Time

| | Time Since Enrollment (MEDI4736 10 mg/kg) | | | |
|---|---|---|---|---|
| | ≥24 wks | ≥16 wks | ≥12 wks | ≥6 wks |
| PD-L1+ | 50% (1/2) | 50% (2/4) | 39% (5/13) | 25% (5/20) |
| PD-L1− | 17% (1/6) | 11% (1/9) | 5% (1/19) | 6% (2/35) |
| Unselected* | 10% (2/20) | 11% (3/27) | 13% (6/47) | 9% (7/75) |

Complete or partial responses (CR/PR) to MEDI4736 were observed in fifty percent of PDL1-positive NSCLC patients treated with 10 mg/kg MEDI4736 for greater than 16-24 weeks (Table 17, below). Early responses to MEDI4736 treatment can be observed in just 6-12 weeks (Table 17).

TABLE 17

Response Rate in PDL1+ NSCLC Patients (MEDI4736, 10 mg/kg)

| | Time Since Enrollment | | | |
|---|---|---|---|---|
| | ≥24 wks (dosed ≤ Nov. 4, 2013) | ≥16 wks (dosed ≤ Dec. 30, 2013) | ≥12 wks (dosed ≤ Jan. 27, 2014) | ≥6 wks (dosed ≤ Mar. 10, 2014) |
| PD-L1+, n | 2 | 4 | 13 | 20 |
| CR/PR, % (n) | 50% (1) | 50% (2) | 38.5% (5) | 25% (5) |

A key driver of response to MEDI4736 is PD-L1+ status

Unselected patients did not show the same high rate of responsiveness to MEDI4736 (Table 18, below).

TABLE 18

Response Rate in Unselected NSCLC Patients (MEDI4736, All Doses)

| | Time Since Enrollment | | | |
|---|---|---|---|---|
| | ≥24 wks (dosed ≤ Nov. 4, 2013) | ≥16 wks (dosed ≤ Dec. 30, 2013) | ≥12 wks (dosed ≤ Jan. 27, 2014) | ≥6 wks (dosed ≤ Mar. 10, 2014) |
| Response Evaluable, n | 31 | 38 | 58 | 87 |
| CR/PR, % (n) | 16.1% (5) | 15.8% (6) | 15.5% (9) | 11.5% (10) |

A summary of Disease Response is provided at Table 19.1 (10 mg/kg Q2W). Where the tumor samples met the criteria for being PDL1-positive, i.e., contained 25% or more tumor cells with PDL1 membrane staining (MSCORE>25%), a 40% response rate was observed in patients treated for at least 16 to 24 weeks or more. A thirty-three percent complete or partial response rate was observed in subjects with squamous cell carcinoma of the head and neck (SCCHN) treated with 10 mg/kg Q2W for at least 16 to 24 weeks or more.

A summary of disease response at all Dose Levels is shown at Table 19.2. Complete or partial response rates were highest in patients that met the criteria for PDL1-positive NSCLC (Table 19.2). A greater benefit was seen in NSCLC and SCCHN at longer treatment times (Table 19.2). Table 19.3 shows a summary of disease response in subjects with dose escalation (Q2W and Q3W).

TABLE 19.1

Summary of Disease Response - 10 mg/kg Q2W

| | | SUBJECTS WITH POTENTIAL FOLLOW-UP OF | | | |
|---|---|---|---|---|---|
| | | =24 Weeks Dosed <= Nov. 4, 2013 | | =16 Weeks Dosed <= Dec. 30, 2013 | |
| | | ALL | EVALUABLE [4] | ALL | EVALUABLE [4] |
| ALL SUBJECTS | N | 55 | 53 | 118 | 112 |
| | CR/PR [1] | 4 (7.3%) | 4 (7.5%) | 10 (8.5%) | 10 (8.9%) |
| | MINOR RESPONSE [2] | 7 (12.7%) | 7 (13.2%) | 15 (12.7%) | 15 (13.4%) |
| | UNCONVENTIONAL RESPONSE [3] | 3 (5.5%) | 3 (5.7%) | 3 (2.5%) | 3 (2.7%) |
| NSCLC | N | 21 | 20 | 29 | 27 |
| | CR/PR [1] | 2 (9.5%) | 2 (10.0%) | 3 (10.3%) | 3 (11.1%) |
| | MINOR RESPONSE [2] | 2 (9.5%) | 2 (10.0%) | 2 (6.9%) | 2 (7.4%) |
| PD-L1 STATUS AVAILABLE ( ) | N | 8 | 8 | 14 | 13 |
| PD-L1 POSITIVE | N | 2 | 2 | 4 | 4 |

TABLE 19.1-continued

Summary of Disease Response - 10 mg/kg Q2W

| | | | | | |
|---|---|---|---|---|---|
| (MSCORE >= 25%) | CR/PR [1] | 1 (50.0%) | 1 (50.0%) | 2 (50.0%) | 2 (50.0%) |
| | MINOR RESPONSE [2] | 1 (50.0%) | 1 (50.0%) | 1 (25.0%) | 1 (25.0%) |
| PD-L1 STATUS AVAILABLE | N | 19 | 18 | 27 | 25 |
| PD-L1 POSITIVE | N | 7 | 7 | 10 | 10 |
| (>=25% OR MEDI >=5%) | CR/PR [1] | 1 (14.3%) | 1 (14.3%) | 2 (20.0%) | 2 (20.0%) |
| | MINOR RESPONSE [2] | 2 (28.6%) | 2 (28.6%) | 2 (20.0%) | 2 (20.0%) |
| PD-L1 STATUS (FRESH) | N | 18 | 17 | 25 | 23 |
| PD-L1 POSITIVE (FRESH) | N | 5 | 5 | 7 | 7 |
| (>=25% OR MEDI >=5%) | CR/PR [1] | 1 (20.0%) | 1 (20.0%) | 1 (14.3%) | 1 (14.3%) |
| | MINOR RESPONSE [2] | 2 (40.0%) | 2 (40.0%) | 2 (28.6%) | 2 (28.6%) |
| PD-L1 NEGATIVE | N | 6 | 6 | 10 | 9 |
| (<25%) | CR/PR [1] | 1 (16.7%) | 1 (16.7%) | 1 (10.0%) | 1 (11.1%) |
| | MINOR RESPONSE [2] | 0 (0.0%) | 0 (0.0%) | 0 (0.0%) | 0 (0.0%) |
| SCCHN | N | 3 | 3 | 15 | 15 |
| | CR/PR [1] | 1 (33.3%) | 1 (33.3%) | 3 (20.0%) | 3 (20.0%) |
| | MINOR RESPONSE [2] | 0 (0.0%) | 0 (0.0%) | 2 (13.3%) | 2 (13.3%) |
| | UNCONVENTIONAL RESPONSE [3] | 1 (33.3%) | 1 (33.3%) | 1 (6.7%) | 1 (6.7%) |

| | | SUBJECTS WITH POTENTIAL FOLLOW-UP OF | | | |
|---|---|---|---|---|---|
| | | =12 Weeks Dosed <= Jan. 27, 2014 | | =6 Weeks Dosed <= Mar. 10, 2014 | |
| | | ALL | EVALUABLE [4] | ALL | EVALUABLE [4] |
| ALL SUBJECTS | N | 166 | 159 | 264 | 246 |
| | CR/PR [1] | 14 (8.4%) | 14 (8.8%) | 18 (6.8%) | 18 (7.3%) |
| | MINOR RESPONSE [2] | 21 (12.7%) | 21 (13.2%) | 38 (14.4%) | 38 (15.4%) |
| | UNCONVENTIONAL RESPONSE [3] | 3 (1.8%) | 3 (1.9%) | 3 (1.1%) | 3 (1.2%) |
| NSCLC | N | 50 | 47 | 84 | 75 |
| | CR/PR [1] | 6 (12.0%) | 6 (12.8%) | 7 (8.3%) | 7 (9.3%) |
| | MINOR RESPONSE [2] | 3 (6.0%) | 3 (6.4%) | 9 (10.7%) | 9 (12.0%) |
| PD-L1 STATUS AVAILABLE ( ) | N | 34 | 32 | 62 | 55 |
| PD-L1 POSITIVE (MSCORE >= 25%) | N | 14 | 13 | 24 | 20 |
| | CR/PR [1] | 5 (35.7%) | 5 (38.5%) | 5 (20.8%) | 5 (25.0%) |
| | MINOR RESPONSE [2] | 1 (7.1%) | 1 (7.7%) | 2 (8.3%) | 2 (10.0%) |
| PD-L1 STATUS AVAILABLE | N | 47 | 44 | 76 | 68 |
| PD-L1 POSITIVE | N | 20 | 19 | 32 | 28 |
| (>=25% OR MEDI >=5%) | CR/PR [1] | 5 (25.0%) | 5 (26.3%) | 5 (15.6%) | 5 (17.9%) |
| | MINOR RESPONSE [2] | 2 (10.0%) | 2 (10.5%) | 3 (9.4%) | 3 (10.7%) |
| PD-L1 STATUS (FRESH) | N | 45 | 42 | 73 | 65 |
| PD-L1 POSITIVE (FRESH) | N | 15 | 14 | 25 | 21 |
| (>=25% OR MEDI >=5%) | CR/PR [1] | 4 (26.7%) | 4 (28.6%) | 4 (16.0%) | 4 (19.0%) |
| | MINOR RESPONSE [2] | 2 (13.3%) | 2 (14.3%) | 2 (8.0%) | 2 (9.5%) |
| PD-L1 NEGATIVE | N | 20 | 19 | 38 | 35 |
| (<25%) | CR/PR [1] | 1 (5.0%) | 1 (5.3%) | 2 (5.3%) | 2 (5.7%) |
| | MINOR RESPONSE [2] | 1 (5.0%) | 1 (5.3%) | 5 (13.2%) | 5 (14.3%) |
| SCCHN | N | 22 | 22 | 44 | 41 |
| | CR/PR [1] | 3 (13.6%) | 3 (13.6%) | 4 (9.1%) | 4 (9.8%) |
| | MINOR RESPONSE [2] | 2 (9.1%) | 2 (9.1%) | 5 (11.4%) | 5 (12.2%) |
| | UNCONVENTIONAL RESPONSE [3] | 1 (4.5%) | 1 (4.5%) | 1 (2.3%) | 1 (2.4%) |

[1] CR/PR: All confirmed and unconfirmed (based on either RECIST for 10 mg/kg or iRRC for other dose-levels)
[2] Minor Response: max reduction in TLs >0-<30% and no PD due to new lesion or NTLs
[3] Unconventional Response: max reduction in TLs >30% & PD due to new lesion
[4] Evaluable population: all patients with disease assessment or died/discontinued due to clinical PD without any disease assessment REFER TO SUPPORTING DATA LISTING(S) 16.3.2.
/SASDATA/cars/dev/medi4736/cd1108/asco02/tables/disresp_mur4.sas DRAFT 18MAY2014 16:54:02

TABLE 19.2

Summary of Disease Response - All Dose Levels

| | | SUBJECTS WITH POTENTIAL FOLLOW-UP OF | | | |
|---|---|---|---|---|---|
| | | ≥24 Weeks Dosed <= Nov. 4, 2013 | | ≥16 Weeks Dosed <= Dec. 30, 2013 | |
| | | ALL | EVALUABLE [4] | ALL | EVALUABLE [4] |
| ALL SUBJECTS | N | 74 | 72 | 138 | 132 |
| | CR/PR [1] | 9 (12.2%) | 9 (12.5%) | 15 (10.9%) | 15 (11.4%) |
| | MINOR RESPONSE [2] | 11 (14.9%) | 11 (15.3%) | 19 (13.8%) | 19 (14.4%) |

TABLE 19.2-continued

Summary of Disease Response - All Dose Levels

|  |  |  |  |  |  |
|---|---|---|---|---|---|
|  | UNCONVENTIONAL RESPONSE [3] | 3 (4.1%) | 3 (4.2%) | 3 (2.2%) | 3 (2.3%) |
| NSCLC | N | 32 | 31 | 40 | 38 |
|  | CR/PR [1] | 5 (15.6%) | 5 (16.1%) | 6 (15.0%) | 6 (15.8%) |
|  | MINOR RESPONSE [2] | 5 (15.6%) | 5 (16.1%) | 5 (12.5%) | 5 (13.2%) |
| PD-L1 STATUS AVAILABLE | N | 8 | 8 | 14 | 13 |
| PD-L1 POSITIVE | N | 2 | 2 | 4 | 4 |
| (MSCORE >=25%) | CR/PR [1] | 1 (50.0%) | 1 (50.0%) | 2 (50.0%) | 2 (50.0%) |
|  | MINOR RESPONSE [2] | 1 (50.0%) | 1 (50.0%) | 1 (25.0%) | 1 (25.0%) |
| PD-L1 STATUS AVAILABLE | N | 24 | 23 | 32 | 30 |
| PD-L1 POSITIVE | N | 8 | 8 | 11 | 11 |
| (>=25% OR MEDI >=5%) | CR/PR [1] | 1 (12.5%) | 1 (12.5%) | 2 (18.2%) | 2 (18.2%) |
|  | MINOR RESPONSE [2] | 2 (25.0%) | 2 (25.0%) | 2 (18.2%) | 2 (18.2%) |
| PD-L1 STATUS (FRESH) | N | 18 | 17 | 25 | 23 |
| PD-L1 POSITIVE (FRESH) | N | 5 | 5 | 7 | 7 |
| (>=25% OR MEDI >=5%) | CR/PR [1] | 1 (20.0%) | 1 (20.0%) | 1 (14.3%) | 1 (14.3%) |
|  | MINOR RESPONSE [2] | 2 (40.0%) | 2 (40.0%) | 2 (28.6%) | 2 (28.6%) |
| PD-L1 NEGATIVE | N | 6 | 6 | 10 | 9 |
| (<25%) | CR/PR [1] | 1 (16.7%) | 1 (16.7%) | 1 (10.0%) | 1 (11.1%) |
|  | MINOR RESPONSE [2] | 0 (0.0%) | 0 (0.0%) | 0 (0.0%) | 0 (0.0%) |
| SCCHN | N | 3 | 3 | 15 | 15 |
|  | CR/PR[1] | 1 (33.3%) | 1 (33.3%) | 3 (20.0%) | 3 (20.0%) |
|  | MINOR RESPONSE [2] | 0 (0.0%) | 0 (0.0%) | 2 (13.3%) | 2 (13.3%) |
|  | UNCONVENTIONAL RESPONSE [3] | 1 (33.3%) | 1 (33.3%) | 1 (6.7%) | 1 (6.7%) |

|  |  | SUBJECTS WITH POTENTIAL FOLLOW-UP OF | | | |
|---|---|---|---|---|---|
|  |  | ≥12 Weeks Dosed <= Jan. 27, 2014 | | ≥6 Weeks Dosed <= Mar. 10, 2014 | |
|  |  | ALL | EVALUABLE [4] | ALL | EVALUABLE [4] |
| ALL SUBJECTS | N | 186 | 179 | 285 | 267 |
|  | CR/PR [1] | 19 (10.2%) | 19 (10.6%) | 23 (8.1%) | 23 (8.6%) |
|  | MINOR RESPONSE [2] | 25 (13.4%) | 25 (14.0%) | 43 (15.1%) | 43 (16.1%) |
|  | UNCONVENTIONAL RESPONSE [3] | 3 (1.6%) | 3 (1.7%) | 3 (1.1%) | 3 (1.1%) |
| NSCLC | N | 61 | 58 | 96 | 87 |
|  | CR/PR [1] | 9 (14.8%) | 9 (15.5%) | 10 (10.4%) | 10 (11.5%) |
|  | MINOR RESPONSE [2] | 6 (9.8%) | 6 (10.3%) | 13 (13.5%) | 13 (14.9%) |
| PD-L1 STATUS AVAILABLE | N | 34 | 32 | 62 | 55 |
| PD-L1 POSITIVE | N | 14 | 13 | 24 | 20 |
| (MSCORE >=25%) | CR/PR [1] | 5 (35.7%) | 5 (38.5%) | 5 (20.8%) | 5 (25.0%) |
|  | MINOR RESPONSE [2] | 1 (7.1%) | 1 (7.7%) | 2 (8.3%) | 2 (10.0%) |
| PD-L1 STATUS AVAILABLE | N | 52 | 49 | 82 | 74 |
| PD-L1 POSITIVE | N | 21 | 20 | 33 | 29 |
| (>=25% OR MEDI >=5%) | CR/PR [1] | 5 (23.8%) | 5 (25.0%) | 5 (15.2%) | 5 (17.2%) |
|  | MINOR RESPONSE [2] | 2 (9.5%) | 2 (10.0%) | 3 (9.1%) | 3 (10.3%) |
| PD-L1 STATUS (FRESH) | N | 45 | 42 | 73 | 65 |
| PD-L1 POSITIVE (FRESH) | N | 15 | 14 | 25 | 21 |
| (>=25% OR MEDI >=5%) | CR/PR [1] | 4 (26.7%) | 4 (28.6%) | 4 (16.0%) | 4 (19.0%) |
|  | MINOR RESPONSE [2] | 2 (13.3%) | 2 (14.3%) | 2 (8.0%) | 2 (9.5%) |
| PD-L1 NEGATIVE | N | 20 | 19 | 38 | 35 |
| (<25%) | CR/PR [1] | 1 (5.0%) | 1 (5.3%) | 2 (5.3%) | 2 (5.7%) |
|  | MINOR RESPONSE [2] | 1 (5.0%) | 1 (5.3%) | 5 (13.2%) | 5 (14.3%) |
| SCCHN | N | 22 | 22 | 44 | 41 |
|  | CR/PR[1] | 3 (13.6%) | 3 (13.6%) | 4 (9.1%) | 4 (9.8%) |
|  | MINOR RESPONSE [2] | 2 (9.1%) | 2 (9.1%) | 5 (11.4%) | 5 (12.2%) |
|  | UNCONVENTIONAL RESPONSE [3] | 1 (4.5%) | 1 (4.5%) | 1 (2.3%) | 1 (2.4%) |

[1] CR/PR: All confirmed and unconfirmed (based on either RECIST for 10 mg/kg or iRRC for other dose-levels)
[2] Minor Response: max reduction in TLs >0-<30% and no PD due to new lesion or NTLs
[3] Unconventional Response: max reduction in TLs >30% & PD due to new lesion
[4] Evaluable population: all patients with disease assessment or died/discontinued due to clinical PD without any disease assessment REFER TO SUPPORTING DATA LISTING(S) 16.3.2.
/SASDATA/cars/dev/medi4736/cd1108/asco02/tables/disresp_mur4.sas DRAFT 18MAY2014 16:54:04

TABLE 19.3

Summary of Disease Response - Dose Escalation Subjects Including Q2W and Q3W

|  |  | SUBJECTS WITH POTENTIAL FOLLOW-UP OF | | | |
|---|---|---|---|---|---|
|  |  | ≥24 Weeks Dosed <= Nov. 4, 2013 | | ≥16 Weeks Dosed <= Dec. 30, 2013 | |
|  |  | ALL | EVALUABLE [4] | ALL | EVALUABLE [4] |
| ALL SUBJECTS | N | 25 | 25 | 26 | 26 |
|  | CR/PR [1] | 5 (20.0%) | 5 (20.0%) | 5 (19.2%) | 5 (19.2%) |
|  | MINOR RESPONSE [2] | 4 (16.0%) | 4 (16.0%) | 4 (15.4%) | 4 (15.4%) |
| NSCLC | N | 13 | 13 | 13 | 13 |
|  | CR/PR [1] | 3 (23.1%) | 3 (23.1%) | 3 (23.1%) | 3 (23.1%) |
|  | MINOR RESPONSE [2] | 3 (23.1%) | 3 (23.1%) | 3 (23.1%) | 3 (23.1%) |
| PD-L1 STATUS AVAILABLE | N | 6 | 6 | 6 | 6 |
| PD-L1 POSITIVE (>=25% OR MEDI >=5%) | N | 2 | 2 | 2 | 2 |

|  |  | SUBJECTS WITH POTENTIAL FOLLOW-UP OF | | | |
|---|---|---|---|---|---|
|  |  | ≥12 Weeks Dosed <= Jan. 27, 2014 | | ≥6 Weeks Dosed <= Mar. 10, 2014 | |
|  |  | ALL | EVALUABLE [4] | ALL | EVALUABLE [4] |
| ALL SUBJECTS | N | 26 | 26 | 27 | 27 |
|  | CR/PR [1] | 5 (19.2%) | 5 (19.2%) | 5 (18.5%) | 5 (18.5%) |
|  | MINOR RESPONSE [2] | 4 (15.4%) | 4 (15.4%) | 5 (18.5%) | 5 (18.5%) |
| NSCLC | N | 13 | 13 | 14 | 14 |
|  | CR/PR [1] | 3 (23.1%) | 3 (23.1%) | 3 (21.4%) | 3 (21.4%) |
|  | MINOR RESPONSE [2] | 3 (23.1%) | 3 (23.1%) | 4 (28.6%) | 4 (28.6%) |
| PD-L1 STATUS AVAILABLE | N | 6 | 6 | 7 | 7 |
| PD-L1 POSITIVE (>=25% OR MEDI >=5%) | N | 2 | 2 | 2 | 2 |

[1] CR/PR: All confirmed and unconfirmed (based on either RECIST for 10 mg/kg or iRRC for other dose-levels)
[2] Minor Response: max reduction in TLs >0-<30% and no PD due to new lesion or NTLs
[3] Unconventional Response: max reduction in TLs >30% & PD due to new lesion
[4] Evaluable population: all patients with disease assessment or died/discontinued due to clinical PD without any disease assessment REFER TO SUPPORTING DATA LISTING(S) 16.3.2.
/SASDATA/cars/dev/medi4736/cd1108/asco02/tables/disresp_mur4.sas DRAFT 18MAY2014 16:54:06

Further patient response rates are shown in FIGS. 25A-C. The response of Non-squamous NSCLC patients and Squamous NSCLC patients to MEDI4736 treatment is shown in FIG. 25A. The response rate relative to tumor PD-L1 status (positive, negative, or NA) is shown in FIGS. 25B and C. The data demonstrate an increased response rate in patients with PD-L1 positive tumors.

Those skilled in the art will recognize, or be able to ascertain using no more than routine experimentation, many equivalents to the specific aspects of the disclosure described herein. Such equivalents are intended to be encompassed by the following claims.

Various publications are cited herein, the disclosures of which are incorporated by reference in their entireties.

Although the foregoing invention has been described in some detail by way of illustration and example for purposes of clarity of understanding, it will be obvious that certain changes and modifications can be practiced within the scope of the appended claims.

SEQUENCE LISTING

SEQ ID NO: 1
>PCT/US2010/058007_77 Sequence 77 from
PCT/US2010/058007 Organism: Homo sapiens
EIVLTQSPGTLSLSPGERATLSCRASQRVSSSYLAWYQQKPGQAPRLLIY
DASSRATGIPDRFSGSGSGTDFTLTISRLEPEDFAVYYCQQYGSLPWTFG
QGTKVEIK

SEQUENCE LISTING

SEQ ID NO: 2
>PCT/US2010/058007_72 Sequence 72 from
PCT/US2010/058007 Organism: Homo sapiens
EVQLVESGGGLVQPGGSLRLSCAASGFTFSRYWMSWVRQAPGKGLEWVAN
IKQDGSEKYYVDSVKGRFTISRDNAKNSLYLQMNSLRAEDTAVYYCAREG
GWFGELAFDYWGQGTLVTVSS SEQ ID NO: 3-VH CDR1
>PCT/US2010/058007_73 Sequence 73 from
PCT/US2010/058007 Organism: Homo sapiens
GFTFSRYWMS SEQ ID NO: 4-VH CDR2
>PCT/US2010/058007_74 Sequence 74 from
PCT/US2010/058007 Organism: Homo sapiens
NIKQDGSEKYYVDSVKG SEQ ID NO: 5-VH CDR3
>PCT/US2010/058007_75 Sequence 75 from
PCT/US2010/058007 Organism: Homo sapiens
EGGWFGELAFDY SEQ ID NO: 6-VL CDR1
>PCT/US2010/058007_78 Sequence 78 from
PCT/US2010/058007 Organism: Homo sapiens
RASQRVSSSYLA SEQ ID NO: 7-VL CDR2
>PCT/US2010/058007_79 Sequence 79 from
PCT/US2010/058007 Organism: Homo sapiens
DASSRAT SEQ ID NO: 8-VL CDR3
>PCT/US2010/058007_80 Sequence 80 from
PCT/US2010/058007 Organism: Homo sapiens
QQYGSLPWT

What is claimed is:

1. A method of treating a patient identified as having non-small cell lung carcinoma (NSCLC), the method comprising administering to the patient 1500 mg of an isolated antibody or an antigen-binding fragment thereof that specifically binds to PD-L1, the isolated antibody or fragment thereof comprising: a VH CDR1 having the amino acid sequence of SEQ ID NO: 3; a VH CDR2 having the amino acid sequence of SEQ ID NO: 4; a VH CDR3 having the amino acid sequence of SEQ ID NO: 5; a VL CDR1 having the amino acid sequence of SEQ ID NO: 6; a VL CDR2 having the amino acid sequence of SEQ ID NO: 7; and a VL CDR3 having the amino acid sequence of SEQ ID NO: 8, wherein at least 25% of the NSCLC tumor cells are PD-L1 positive.

2. The method of claim 1, wherein the administration is repeated every 14 to 21 days.

3. The method of claim 2, wherein the administration is repeated every 14 days.

4. The method of claim 1, wherein the NSCLC is refractory to at least one chemotherapeutic agent.

5. The method of claim 4, wherein the chemotherapeutic agent is Vemurafenib, Afatinib, Cetuximab, Carboplatin, Bevacizumab, Erlotinib, or Pemetrexed.

6. The method of claim 1, wherein the NSCLC is a squamous cell carcinoma.

7. The method of claim 1, wherein the NSCLC is a non-squamous cell carcinoma.

8. The method of claim 1, wherein PD-L1 status is detected using immunohistochemistry.

9. The method of claim 1, wherein the isolated antibody or fragment thereof comprises a VL having the amino acid sequence of SEQ ID NO: 1; and a VH having the amino acid sequence of SEQ ID NO: 2.

* * * * *

SEQUENCE LISTING

<160> NUMBER OF SEQ ID NOS: 8

<210> SEQ ID NO 1
<211> LENGTH: 108
<212> TYPE: PRT
<213> ORGANISM: Homo sapiens

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105

<210> SEQ ID NO 2
<211> LENGTH: 121
<212> TYPE: PRT
<213> ORGANISM: Homo sapiens

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
            115                 120

<210> SEQ ID NO 3
<211> LENGTH: 10

```
<212> TYPE: PRT
<213> ORGANISM: Homo sapiens

<400> SEQUENCE: 3

Gly Phe Thr Phe Ser Arg Tyr Trp Met Ser
1               5                   10

<210> SEQ ID NO 4
<211> LENGTH: 17
<212> TYPE: PRT
<213> ORGANISM: Homo sapiens

<400> SEQUENCE: 4

Asn Ile Lys Gln Asp Gly Ser Glu Lys Tyr Tyr Val Asp Ser Val Lys
1               5                   10                  15
Gly

<210> SEQ ID NO 5
<211> LENGTH: 12
<212> TYPE: PRT
<213> ORGANISM: Homo sapiens

<400> SEQUENCE: 5

Glu Gly Gly Trp Phe Gly Glu Leu Ala Phe Asp Tyr
1               5                   10

<210> SEQ ID NO 6
<211> LENGTH: 12
<212> TYPE: PRT
<213> ORGANISM: Homo sapiens

<400> SEQUENCE: 6

Arg Ala Ser Gln Arg Val Ser Ser Ser Tyr Leu Ala
1               5                   10

<210> SEQ ID NO 7
<211> LENGTH: 7
<212> TYPE: PRT
<213> ORGANISM: Homo sapiens

<400> SEQUENCE: 7

Asp Ala Ser Ser Arg Ala Thr
1               5

<210> SEQ ID NO 8
<211> LENGTH: 9
<212> TYPE: PRT
<213> ORGANISM: Homo sapiens

<400> SEQUENCE: 8

Gln Gln Tyr Gly Ser Leu Pro Trp Thr
1               5
```